US011587677B2

(12) United States Patent
Gillies et al.

(10) Patent No.: US 11,587,677 B2
(45) Date of Patent: Feb. 21, 2023

(54) PREDICTING INTENSIVE CARE TRANSFERS AND OTHER UNFORESEEN EVENTS USING MACHINE LEARNING

(71) Applicant: THE REGENTS OF THE UNIVERSITY OF MICHIGAN, Ann Arbor, MI (US)

(72) Inventors: Christopher Elliot Gillies, Ann Arbor, MI (US); Daniel Francis Taylor, Belleville, MI (US); Kevin R. Ward, Superior Township, MI (US); Fadi Islim, Ypsilanti, MI (US); Richard Medlin, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 503 days.

(21) Appl. No.: 16/691,123

(22) Filed: Nov. 21, 2019

(65) Prior Publication Data
US 2020/0160998 A1   May 21, 2020

Related U.S. Application Data

(60) Provisional application No. 62/770,315, filed on Nov. 21, 2018.

(51) Int. Cl.
| G16H 50/20 | (2018.01) |
| G06K 9/62 | (2022.01) |
| G16H 10/60 | (2018.01) |

(52) U.S. Cl.
CPC .............. *G16H 50/20* (2018.01); *G06K 9/623* (2013.01); *G06K 9/6257* (2013.01); *G06K 9/6264* (2013.01); *G16H 10/60* (2018.01)

(58) Field of Classification Search
CPC ........ G16H 50/20; G16H 10/60; G16H 10/40; G16H 50/30; G06K 9/623; G06K 9/6257; G06K 9/6264
See application file for complete search history.

(56) References Cited

U.S. PATENT DOCUMENTS

| 8,092,380 B2 | 1/2012 | Rothman et al. |
| 8,100,829 B2 | 1/2012 | Rothman et al. |
| 8,355,925 B2 | 1/2013 | Rothman et al. |
| 8,403,847 B2 | 3/2013 | Rothman et al. |
| 8,454,506 B2 | 6/2013 | Rothman et al. |
| 11,257,574 B1 * | 2/2022 | Boussios ................ G16H 50/30 |

(Continued)

OTHER PUBLICATIONS

Churpek et al., "Using Electronic Health Record Data to Develop and alidate a Prediction Model for Adverse Outcomes on the Wards," *Crit Care Med.*, 42(4):841-848 (Apr. 2014).

(Continued)

*Primary Examiner* — Edward F Urban
*Assistant Examiner* — Wassim Mahrouka
(74) *Attorney, Agent, or Firm* — Marshall, Gerstein & Borun LLP

(57) ABSTRACT

A method of predicting patient deterioration includes receiving an electronic health record data set of the patient, determining a risk score corresponding to the patient by analyzing the electronic health record data set of the patient using a trained machine learning model, determining a threshold value using an online/reinforcement learning model, comparing the risk score to the threshold value, and when the risk score exceeds the threshold value, generating an alarm. A non-transitory computer readable medium includes program instructions that when executed, cause the computer to receive a list of patients, display selectable patient information corresponding to each of the list of patients according to an ordering established by a feature importance algorithm, receive a selection, retrieve vital sign information corresponding to the selection, and display the vital sign information.

20 Claims, 14 Drawing Sheets

(56) References Cited

U.S. PATENT DOCUMENTS

| | | | | |
|---|---|---|---|---|
| 2014/0074509 A1* | 3/2014 | Amarasingham | ...... | G16H 50/70 |
| | | | | 705/3 |
| 2014/0074510 A1* | 3/2014 | McClung | ............... | G16H 50/30 |
| | | | | 705/3 |
| 2014/0302172 A1* | 10/2014 | Schaab | ............ | G01N 33/56966 |
| | | | | 435/7.1 |
| 2016/0378943 A1* | 12/2016 | Vallée | ..................... | G16H 40/63 |
| | | | | 705/2 |
| 2017/0249434 A1* | 8/2017 | Brunner | ................ | G06F 16/258 |
| 2019/0287661 A1* | 9/2019 | Nobre | ..................... | G16H 40/63 |
| 2020/0051695 A1* | 2/2020 | Sevenster | .............. | G16H 10/60 |
| 2022/0051773 A1* | 2/2022 | Appelbaum | ............ | G16H 20/10 |

OTHER PUBLICATIONS

Churpek et al., "Multicenter development and validation of a risk stratification tool for ward patients," *Am J Respir Crit Care Med.*, 190(6):649-655 (Sep. 2014).

Rothman et al., "Development and validation of a continuous measure of patient condition using the Electronic Medical Record," *J of Biomedical Informatics.*, 46(5):837-848 (Dec. 2013).

Lundberg et al., "A unified approach to interpreting model predictions," *Advances in Neural Information Processing Systems 30*, pp. 4765-4774 (2017).

Lundberg et al., "Consistent Individualized Feature Attribution for Tree Ensembles," KDD's, pp. 1-9 (2018).

Young et al., "Inpatient transfers to the intensive care unit: delays are associated with increased mortality and morbidity," *J Gen Intern Med.*,18(2):77-83 (2003).

\* cited by examiner

500

| PICTURE | MCIRCC |
|---|---|
| ID | PICTURE |
| ID: 51A0A29A-027D-E711-80DD-0025B5000026<br>MRN: 000000000<br>DOB: SEPTEMBER 29, 1983<br>NAME: DOE, JOHN |  |
| ID: C01422D9-2092-E611-80D0-0025B5000026<br>MRN: 000000000<br>DOB: SEPTEMBER 29, 1983<br>NAME: DOE, JOHN |  |
| ID: 0B78AF5A-31CB-E711-80E8-3890A57FC706<br>MRN: 000000000<br>DOB: SEPTEMBER 29, 1983<br>NAME: DOE, JOHN |  |
| ID: B858CD96-3609-E511-846C-F0921C021BF8<br>MRN: 000000000<br>DOB: SEPTEMBER 29, 1983<br>NAME: DOE, JOHN | 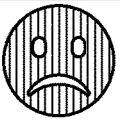 |
| ID: DC7F8AF1-BAE4-E211-9FAA-00215A9B0094<br>MRN: 000000000<br>DOB: SEPTEMBER 29, 1983<br>NAME: DOE, JOHN | 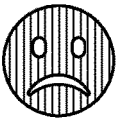 |
| ID: C69F70B4-CED2-E211-9FAA-00215A9B0094<br>MRN: 000000000<br>DOB: SEPTEMBER 29, 1983<br>NAME: DOE, JOHN |  |
| ID: DC567D32-0A86-E411-B478-F0921C021BF8<br>MRN: 000000000<br>DOB: SEPTEMBER 29, 1983<br>NAME: DOE, JOHN |  |
| ID: 855F8903-74F0-E611-80D6-0025B5000026<br>MRN: 000000000<br>DOB: SEPTEMBER 29, 1983<br>NAME: DOE, JOHN |  |

PREDICTING INTENSIVE CARE TRANSFERS AND OTHER UNFORESEEN EVENTS USING MACHINE LEARNING

CROSS-REFERENCE TO RELATED APPLICATION

The present application claims priority to U.S. patent application No. 62/770,315, filed Nov. 21, 2018. The priority application is hereby incorporated by reference.

FIELD OF THE DISCLOSURE

The present disclosure generally relates to a system and method for predicting intensive care transfers and other unforeseen events using machine learning, more particularly, to machine learning methods and systems for analyzing data to predict patient deterioration.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Identifying patient deterioration on general hospital wards is a challenge for clinicians. Early detection of patient deterioration has been found to lead to a 3.5 times reduced mortality risk, five-day reduction in length of hospital stay, and over $13,000 in reduced costs per patient/episode. Past attempts to quantify patient risk include rule-based scores such as the Modified Early Warning Score (MEWS) and the Rothman Index. Recently, statistical learning systems such as Electronic Cardiac Arrest Risk Triage (eCART) have been developed to address this need. However, these rule-based scoring and statistical learning systems result in too many false alarms, and do not reliably predict patient deterioration. Furthermore, existing systems do not leverage the power of nonlinear models to make automatically explicable predictions. As such, clinicians may not want to use the existing approaches to make clinical decisions due to lack of confidence.

BRIEF SUMMARY

In one aspect, a method of predicting patient deterioration includes receiving an electronic health record data set of the patient, determining a risk score corresponding to the patient by analyzing the electronic health record data set of the patient using a trained machine learning model, determining a threshold value using an online/reinforcement learning model, comparing the risk score to the threshold value, and when the risk score exceeds the threshold value, generating an alarm.

In another aspect, a non-transitory computer readable medium containing program instructions that when executed, cause the computer to receive a list of patients, each including a respective risk score, display patient information corresponding to each of the list of patients in a display device, wherein the patient information is selectable, and wherein the each of the list of patients is displayed in an ordering established by a feature importance algorithm, receive a selection corresponding to one of the each of the list of patients, retrieve vital sign information corresponding to the selected one of the each of the list of patients, and display the vital sign information in the display device.

BRIEF DESCRIPTION OF THE DRAWINGS

FIG. 5A depicts a graphical user interface for viewing patient vital information corresponding to a plurality of patients.

FIG. 5B depicts a graphical user interface for viewing patient vital information.

DETAILED DESCRIPTION

Overview

Figure 1:
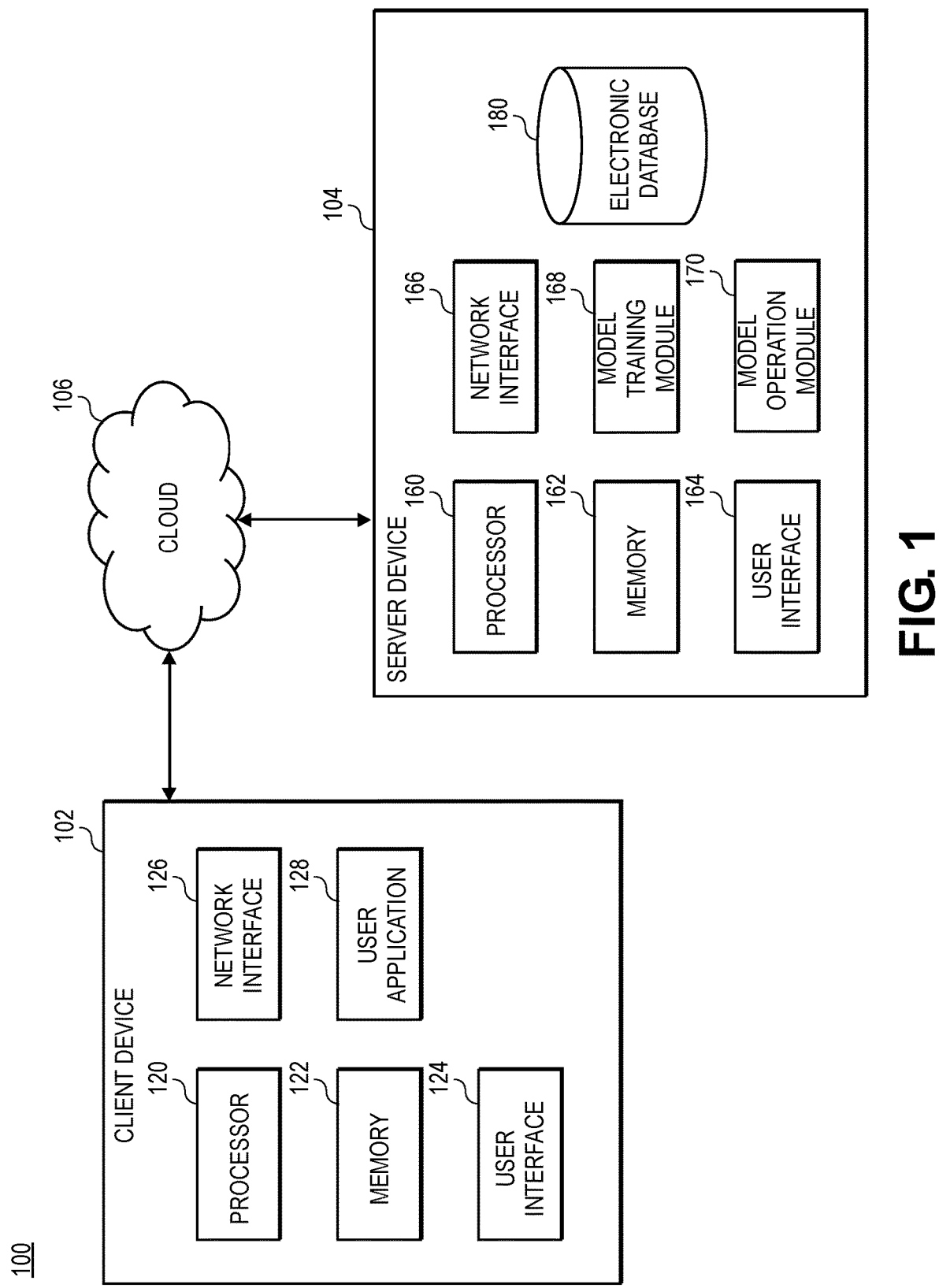
FIG. 1 depicts an example environment for training, operating, and tuning ML models, according to one embodiment and scenario.

The present techniques include methods and systems for quantifying patient/care receiver risk to assist clinicians/care givers in identifying deteriorating patients. Herein, a "care receiver" may be any person receiving the care of any care giver. For example, a care receiver may be a patient (inpatient or outpatient) in any clinic, hospital, or other setting; or a person receiving care in another setting such as a nursing home, a home care facility, a rehabilitation facility, etc. A clinician may be a nurse (e.g., a Registered Nurse or Certified Nurse Assistant), a physician (e.g., a Physician's Assistant), medical doctor, specialist, or another type of care giver (e.g., a Cardiologist, Radiologist, a home care provider, etc.). Herein the terms "care giver" and "clinician" may be used interchangeably. The terms "care receiver" and "patient" may be used interchangeably. "Care" may include any observation (e.g., visual or instrument-based monitoring of a care receiver, including computer-based instrumentation) and/or hands-on intervention performed by a care giver.

The present techniques include reinforcement learning (RL) techniques (e.g., a method of adaptive threshold tuning (ATT)) enabling classifiers to dynamically update a prediction threshold based on clinician behavior. Some embodiments of the present techniques include a technique, Predicting Intensive Care Transfers and other Unforeseen Events that predicts patient deterioration (e.g., ICU transfer, rapid response team activation, and/or death) better than existing methods. For example, the present techniques may include fewer false alarms and predictions that include an explanation of the top reasons for the prediction(s) that a clinician interpreting the results of the technique may use in their decision-making.

In some embodiments, the present techniques utilize ATT (e.g., an RL or online learning algorithm) that can be applied to any classifier predicting patient risk. The present techniques may use a state of the art machine learning (ML) technique (e.g., deep learning) that demonstrates a higher positive predictive value (PPV) for a given level of sensitivity compared to any existing measure of patient deterioration. The present techniques also possess the ability to automatically generate explanations/interpretations for predictions generated by nonlinear models used in the present techniques using feature importance algorithms (e.g., SHapley Additive exPlanation (SHAP) value analysis). The present techniques may be seamlessly integrated into any hospital system using available hardware. Implementing the present techniques, with or without ATT, requires minimal change to the clinician's current workflow.

In some embodiments, the present techniques include a gradient boosting tree algorithm created utilizing electronic health record (EHR) data to predict ICU transfer or death as a proxy for patient deterioration. In another embodiment, the present techniques use a deep learning model. In general, the present techniques include more accurate and explicable techniques than those known in the art. Predictions generated using the present techniques may include an explanation of the main factors contributing to predictions generated in the present techniques with respect to individual patients. Furthermore, the prediction threshold may be adapted based on individual clinician behavior. Further still, the use of a nonlinear, tree-based classifier by the present techniques to predict patient outcomes as well as explaining the main factors influencing the prediction of a patient outcome is not known in the art. In general the present techniques make passive predictions of patient deterioration, in that no extra work is required on the part of the clinician, and no changes are necessary to the care environment (e.g., the hospital). As noted above, whereas current measures of patient deterioration are simple rule based predictors (e.g., MEWS, Rothman Index) or linear classifiers (e.g., eCart), the present techniques utilize state of the art techniques (e.g., ML) and provides additional expository information. The use of nonlinear models to form predictions, and the ability to automatically generate explanations of those predictions, is not known in the art.

Example Computing Environment

FIG. 1 depicts an example computing environment 100 for implementing the present techniques (e.g., training, operating, and tuning ML (e.g., ATT) models), according to one embodiment and scenario. The environment 100 may include a client device 102 associated with a server device 104, and a network 106.

The client 102 is remote from the server 104 and is coupled to the server 104 via the network 106. The network 106 may include any suitable combination of wired and/or wireless communication networks, such as one or more local area networks (LANs), metropolitan area networks (MANs), and/or wide area network (WANs). As just one specific example, the network 106 may include a cellular network, the Internet, and a server-side LAN. As another example, the network may support a cellular (e.g., 4G) connection to a mobile device of a user and an IEEE 802.11 connection to the client 102. While referred to herein as a "server," the server 104 may, in some implementations, include multiple servers and/or other computing devices. Moreover, the server 104 may include multiple servers and/or other computing devices distributed over a large geographic area (e.g., including devices at one or more data centers), and any of the operations, computations, etc., described below may be performed in by remote computing devices in a distributed manner. In some embodiments, multiple clients and/or servers may be used by different parties. For example, in an embodiment, a clinician may use a first client 102, and a patient may use a second client 102, wherein the first client and the second client include different sets of functionality provided by different sets of computer-executable instructions and/or different hardware configurations. In an embodiment, a clinician may use a first client 102 and an operator may use a second client 102, wherein the clinician uses the first client to access a user interface including predictions and/or explanations, as discussed herein, and the operator uses the second client 102 to train, configure, tune, and/or operate one or more ML models.

The client 102 may include hardware and software components. For example, the client 102 may be implemented using a mobile computing device (e.g., a smart phone). The client 102 may include computer-executable instructions for retrieving/receiving data for rendering in a graphical user interface (GUI) and/or rendered GUI elements (e.g., images, widgets, executable code, etc.). In some cases, the client 102 may be implemented in a laptop, tablet, or wearable device. The client 102 may include a processor 120, a memory 122, an input/output user interface 124, a network interface 126, and a user application 128. The processor 120 may be a single processor (e.g., a central processing unit (CPU)), or may include a set of processors (e.g., a CPU and a graphics processing unit (GPU)). The client 102 may include further components, in some use cases. In some embodiments, the client 102 may include one or more microphones and/or video display/recording devices. The client 102 may include a vibrational element, such as a vibration motor.

In an embodiment, a sequence may include a clinician viewing or otherwise noting an alarm corresponding to a patient. The clinician may then inspect plotted explanations of vitals that are ordered by the most important metric according to a feature importance algorithm, as described below. When the explanations suggest a physiological problem relating to the patient, the clinician will act accordingly. When the explanations do not suggest a physiological issue, the clinician can be confident in their decision to ignore, delay, and/or suppress the alarm.

The memory 122 may be a computer-readable, non-transitory storage unit or device, or collection of units/devices, that may include persistent (e.g., hard disk) and/or non-persistent memory components. The memory 122 may store instructions that are executable on the processor 120 to perform various operations, including the instructions of various software applications (e.g., the user application 128) and data generated, received and/or retrieved by such applications. In the example implementation of FIG. 1, the memory 122 stores at least a user application 128. Generally, the user application 128 is executed by the processor 120 to facilitate bidirectional transmission of user interface data between the client 102 and the server 104 (e.g., receiving ML output data from the server 104, sending user interface events/inputs to the server 104, etc.).

The user interface 124 includes hardware, firmware and/or software configured to enable a user to interact with (i.e., both provide inputs to and perceive outputs of) the client 102. For example, the user interface 124 may include a touchscreen with both display (e.g., video display device) and manual input capabilities. Alternatively, or in addition, the user interface 124 may include a keyboard for accepting user inputs, and/or a microphone (with associated processing components) that provides voice control/input capabilities to the user. The user interface 124 may include a combination of peripheral devices (e.g., a keyboard and mouse) and one or more display screens. In some embodiments, the client 102 may include multiple different implementations of the user interface 124 (e.g., a first user interface 124 for displaying patient risk scores and a second user interface 124 for displaying thresholds).

The network interface 126 includes hardware, firmware and/or software configured to enable the client 102 to exchange electronic data with the server 104 via the network 106 via a wired and/or wireless connection. For example, the network interface 126 may include a cellular communication transceiver, a WiFi transceiver, transceivers for one or more other wireless communication technologies (e.g., 4G), a wired Ethernet adapter, etc.

In some embodiments, the user application 128 (or other software stored in the memory 122) provides functionality for displaying the output of ML models and for receiving user input and for sending that user input to the server 104. For example, if the client 102 is a smartphone, then the user application 128 may be an application specific to a particular mobile computing platform (e.g., an Android, iPhone or other device). The user application 128 may include computer-executable instructions for rendering one or more GUI screens via the user interface 124, receiving/retrieving information (e.g., map data) and for displaying the information in the GUI screens. The GUI screens may be interactive and may allow the user to perform various functions. For example, the user application 128 may allow the user to select from a menu of options displayed in a GUI screen, by, for example, using one or more of the user's digits. The user application 128 may allow the user to type in values (e.g., text or numeric data) using a software keyboard. In some embodiments, hardware events (e.g., mouse scrolling or clicks) may be input by the user. The GUI may accept keystroke and mouse input events of the user, and may process the events and/or transmit the events to a server for processing. The user interface 124 may perform the low-level task of receiving the user's input events from a device (e.g., a touch screen) and may dispatch those events to the user application 128 for processing. In general, the user application 128 allows a user to access the features of the user application 128 without performing any programming.

The server 108 may include hardware and software components. For example, the server 108 may be implemented using one or more server devices. The server 108 includes a processor 160, a memory 162, a user application 164, a network interface 166, a model training module 168, a model operation module 170, and an electronic database 180. The server 104 may include further components. The server 108 may include computer-executable instructions for retrieving/receiving data relating to the training and/or operation of models (e.g., EHR data). The server 108 may also include instructions for receiving requests from the client 102 via the network 106 for particular data and/or instructions for receiving responses from the client 102 including parameters (e.g., HTTP POST requests including electronic form data). The server 108 may retrieve data via the client 102 or the database 180.

The processor 160 may be a single processor (e.g., a central processing unit (CPU)), or may include a set of processors (e.g., a CPU and a graphics processing unit (GPU)). The memory 162 is a computer-readable, non-transitory storage unit or device, or collection of such units/devices, that may include persistent (e.g., hard disk) and/or non-persistent memory components. The memory 162 may store data generated and/or used by the user application 164, the model training module 168, and the model operation module 170, for example. The memory 162 may also store trained and/or untrained models, and information retrieved from the electronic database 180.

The user application 164 may be an application configured to mediate communication between the client 102 and the server 104. Specifically, the user application 164 may be an application (e.g., a web application executed by a web server) that includes one or more application programming interfaces (APIs). The user application 164 may receive HTTP requests (e.g., GET and/or POST requests) from the user application 128. The requests may include parameters (e.g., dates, times, query commands/parameters, etc.). The user application 164 may issue HTTP responses to the user application 128 that may include response data.

The network interface 166 includes hardware, firmware and/or software configured to enable the server 104 to exchange electronic data with the client 102 via the network 106 via a wired and/or wireless connection. For example, the network interface 166 may include a cellular communication transceiver, a WiFi transceiver, transceivers for one or more other wireless communication technologies (e.g., 4G), a wired Ethernet adapter, etc.

The model training module 168 is generally configured to train models (e.g., ML models). For example the model training module 168 may include a set of computer-executable instructions that when executed by the processor 160 cause the server device 104 to retrieve data (e.g., a training data set) from the electronic database. The instructions may further cause the model training module 168 to train a model using the training data set by, for example, analyzing each element of the training data set using a model training algorithm. The model training module 168 may instantiate an untrained model, load the untrained model into the memory 162, and train the model while the model is loaded in the memory 162. Once the model is trained, the model training module 168 may write the model (e.g., as a serialized object and/or a blob of binary data) to the electronic database 180. The model training module 168 may also save parameters (e.g., weights or other model metadata) to the electronic database 180, in association with the trained model. The trained model may be retrieved from the electronic database 180 by another component (e.g., the model operation module 170).

The model operation module 170 may load a trained model by selecting it from the electronic database 180 or the memory 162. The model operation module 170 may initialize the trained model using the associated parameters. The model operation module 180 may receive and/or retrieve input from the server 102. For example, the user application 164 may receive a user request for data that requires the operation of the model operation module 170. The user application 164 may pass the request to the model operation module 170, which may invoke the required model, returning the output of the invoked model to the user application 164.

The database 180 may be any suitable database (e.g., a structured query language (SQL) database, flat-file database, key/value store, or a proprietary database or legacy system).

The database 180 may store trained models, model parameters, patient information, EHR data, etc., and may allow other components (e.g., the user application 164) to query the stored information.

Example Provision of Care

Figure 2A:
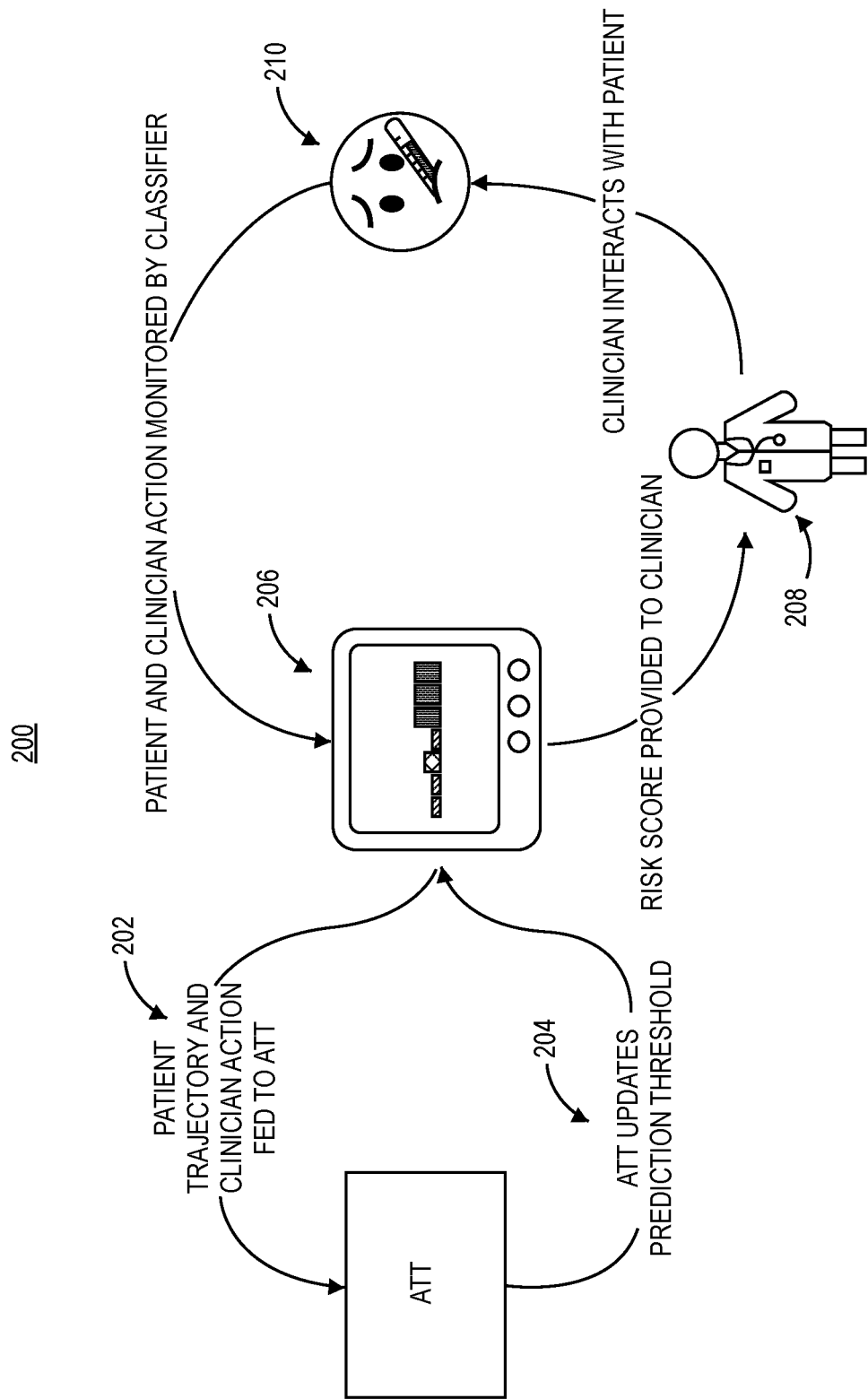
FIG. 2A is a flow diagram depicting an example method of using a tuning algorithm in the provision of care.

FIG. 2A depicts an example flow diagram representing an example method 200 for the provision of care using the system 100 of FIG. 1. FIG. 2A may include feeding patient trajectory and clinician action into an ATT (block 202). The ATT may be trained by the model training module 168, and may be operated by the model operation module 170. The patient trajectory may be retrieved from the electronic database 180 and/or the client device 102 (e.g., from the user application 128) via the network 106. The clinician action may be an input (e.g., an event received via the user interface 124) that the user application 128 passes to the user application 164 via the network 106. For example, the input may correspond to an indication of a care recipient's condition and/or an intervention of a clinician. The input may be entered by a clinician or other care provider into the user interface 124. Possible inputs include, without limitation, the prescribing and/or ordering of any therapy (e.g., any medication including antibiotics, a fluid bolus, an intravenous drip, Oxygen, vasoactive medication administration, dialysis, opioid administration, antiarrhythmic administration, naloxone administration, etc.). The present techniques may determine that a therapy is applied to a particular patient by reference to a specific code and/or the presence of an order in a computerized data record of the patient (e.g., in an EHR). The input may indicate a transfer of a patient (e.g., to an ICU).

In some embodiments, the system 100 may associate at least one input with a ratio or other measurement acting as a threshold. For example, the system 100 may be programmed to consider an input of equal to or more than 10 liters of oxygen in a three hour period to constitute an intervention. Such ratios may be configurable, and may be stored in the electronic database 180. The system 100 may also be programmed to calculate such ratios relative to patient characteristics (e.g., the age of a patient).

The method 200 may include prompting the clinician to input an indication of whether an intervention was provided for a care receiver, and updating an alarm threshold based on the clinician's indication (block 204). In general, over time, the ATT (e.g., RL algorithm) learns a threshold based on responses/indications provided by the clinician. The indication may be a Boolean value (e.g., "yes" or "no"), or the clinician/care giver may be prompted to choose one or more values from a menu using a graphical user interface widget (e.g., a slider mechanism). In some embodiments, to limit the amount of additional work required by the clinician, the user application 128 may only prompt the clinician to enter information at prescribed times (e.g., at the end of a clinician's shift). The prompt may be issued to the clinician by the user application 128 via user interface 124. For example, user application 128 may include instructions for issuing the prompt based on a condition (e.g., a timer, a geographic-based condition, a movement detected by an accelerometer of the client device 102, etc.).

The indication of the clinician may be provided to the model training module 168 to re-train the model (e.g., to update to the alarm threshold). In such cases, the model operation module 170 may take the model offline (i.e., cease execution of the instructions relating to operating the model). The model operation module 170 may only take the model offline very briefly in some embodiments (e.g., for one second), during which time period the model training module 168 may update the model). The model operation module 170 may then reload the updated model into the memory 162, whereupon the clinician (via the client device 102) may once again access the model. In another embodiment, the model training module 168 may include instructions for updating the model online (i.e., while the model is being operated by the model operation module 170). To update the model online, the user application 128 may provide the indication of the clinician to the server device (e.g., to the user application 164). The user application 164 may include instructions for updating the mode (e.g., by calling an updateClassifier( ) function of the model operation module 170, providing the clinician's indication as a parameter). In some embodiments, the model training module 168 may train the model using an online gradient descent algorithm, wherein the algorithm may make updates to a threshold associated with the model based on one data point at a time.

As noted above, in some embodiments, ATT (e.g., an RL technique) may be employed. In addition to online learning, RL and deep reinforcement learning (DRL) are methodologies that can take as input the complex series of patient-clinician interactions and the abundance data contained within the EHR to tune the alarm threshold for a classifier. RL is well-suited for the problem of learning the correlation between immediate action (e.g., a clinician giving an antibiotic or fluids to a patient) and a delayed response (e.g. the patient recovering without needing to be transferred to the ICU). Traditionally, RL depends on being able to identify all possible states a patient could be in, as well as all possible actions that could be taken on the patient (e.g., given fluids, given antibiotics, put on vasopressors, etc.) and how those actions affected the patient. In some embodiments, artificial neural networks can be used to learn the map from patient-state, clinician-action pair to outcome. An embodiment of ATT could use such a system to monitor patient trajectory and clinical action and update the alarm threshold. While the present techniques are described in some embodiments herein as using a gradient boosting tree, it should also be noted that other embodiments may include deep learning models and/or recurrent models (e.g. artificial neural networks or Long-Short Term Memory (LSTM) networks). Additional information regarding techniques for training the model is provided below.

The method 200 may further include generating a risk score based on the updated model (block 206). The model operated by the model operating module 170 may generate the risk score. The risk score may be transmitted by the server device (e.g., by the user application 164) to the client 102 (e.g., to the user application 128).

The method 200 may include providing the risk score to the clinician (block 208). The client 102 may present the risk score to the clinician. For example, the user application 128 may include computer-executable instructions for displaying the risk score may be presented in a graphical view (e.g., via user interface 124) that the clinician may interpret and interact with, as depicted below. In other embodiments, the user application 128 may provide the risk score to the clinician using another suitable method (e.g., via email, text message, etc.). In some cases, a module of the server (e.g., an email server, the user application 168, etc.) may provide the risk score to the clinician via the network 106 without the use of the client 102.

The method 200 may include collecting data relating to the clinician's interactions with the patient (block 210). For example, the clinician may observe the patient, intervene in the patient's care, adjust the patient's existing care, etc. The clinician's actions and/or observations may be captured by a device, such as the client 102. For example, the clinician may carry the client 102 as the clinician visits patients or otherwise provides care. The physician may access the client 102 to enter information regarding the status of the patient and any action taken by the clinician. For example, the clinician may enter notes, speech recordings, or other suitable data inputs via the user interface 124. The clinician's input may be transmitted by the user application 128 via the network 106 to the server 104, whereupon the input may be used in the model training module 168 and/or the model operation module 170 to refine the model (e.g., by updating the threshold values in an ATT model).

While ATT can be applied to any classifier attempting to predict patient deterioration, known techniques are limited due to low PPV. The present techniques include methods and systems for predicting patient deterioration that demonstrate a much higher PPV for a given level of sensitivity than any method currently available. In what follows, additional examples are provided of deploying ATT models in the context of the present techniques.

Exemplary Model Development Methods

In an embodiment, EHR data is used to build a model. A first volume of data (e.g., spanning two or more years) may be used. The first volume of data is divided into a training data set and validation/parameter tuning data set according to a 90/10 split. In some cases, other suitable splits may be used. A second volume of data spanning a disjoint time period of the data in the training data set and the validation/parameter tuning data set (e.g., data from another calendar year) may be used to evaluate the performance of the present techniques.

Figure 2B:
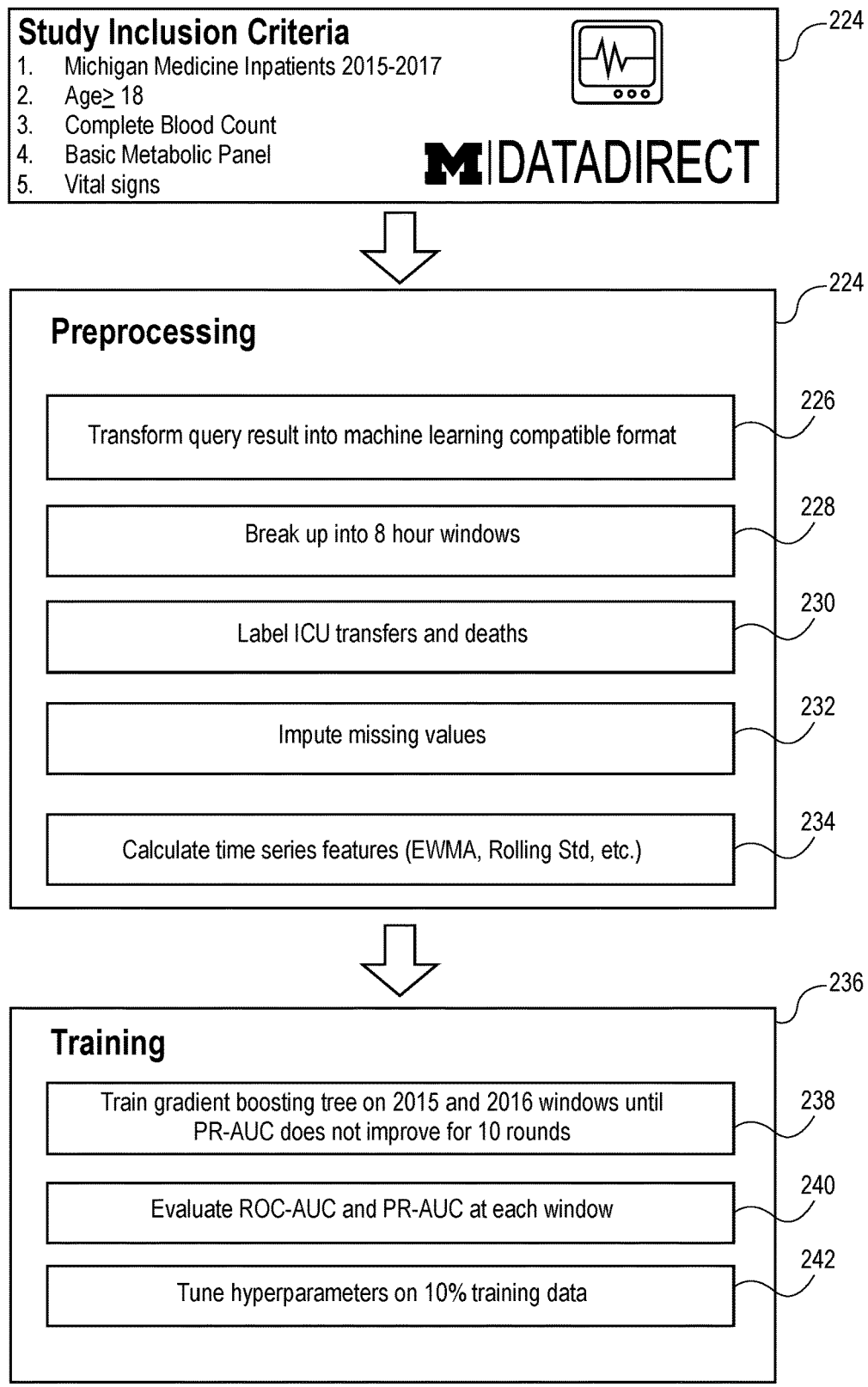
FIG. 2B is a flow diagram depicting an example data processing and training pipeline method.

FIG. 2B depicts a data processing and training pipeline method 220 for implementing the present techniques. The pipeline method 220 may include gathering study participant EHR data based on a number of criteria (block 222).

In a preferred embodiment, the EHR data may include EHR data relating to each respective adult patient. The EHR data may include vital signs (e.g., pulse oximetry derived hemoglobin oxygen saturation, heart rate, blood pressure, respiratory rate), complete blood counts (e.g., mean platelet volume, hematocrit, hemoglobin, mean corpuscular hemoglobin, mean corpuscular hemoglobin concentration, mean corpuscular hemoglobin volume, white blood cell count, platelets, red blood cell count, and red cell distribution width), basic metabolic panel (e.g., blood urea nitrogen, potassium, sodium, glucose, chloride, CO2, calcium, creatinine), demographics (e.g., age, weight, race and gender, zip code), less common labs (e.g., bilirubin, partial thromboplastin time, international normalized ratio, lactate, magnesium and phosphorous), and any other suitable patient indicators now existing or later developed (e.g., use of O2, Glasgow Coma Score or components thereof, and urine output over past 24 hours, antibiotic administration, blood transfusion, fluid administration, etc.); and calculated values including shock index and mean arterial pressure. The EHR data may additionally or alternatively include chronic medical and/or surgical conditions.

It should be appreciated that as new signals (e.g., EHR data relating to each patient) are identified, those signals may be added to the EHR data. It also should be appreciated that in some embodiments, other cohorts may be selected to suit certain predictive imperatives. For example, a data set relating to a cohort of individuals under the age of 12 may be constructed, and/or a data set relating to a cohort of male patients aged 65-90.

The pipeline method 220 may include preprocessing the EHR data (block 224). The pipeline method 220 may include transforming query results into an ML-compatible format (block 226). The pipeline method 200 breaking up the EHR into windowed time intervals (e.g., eight-hour windows) (block 228). Continuing the above example, each EHR data set corresponding to each respective adult may include time-series data. For example, data representing various EHR data throughout a patient's day may be represented in the EHR data set. The EHR data set may include lab results and other information taken at various times of the day. Therefore, lab results among the patients represented by the EHR data may be non-uniform. To normalize patient EHR data, for uniform analysis, the present techniques may subdivide each patient's time in the care setting (e.g., hospital, home or other facility) into discrete time intervals (e.g., 8-hour intervals), also referenced herein as "windows." A "window" may be defined by reference to a pre-determined period of time (e.g., an n-minute window) wherein n is any positive integer. In some embodiments, a window may be a smaller interval of time (e.g., one second or less). A "window" may be determined according to a fixed time division, or in accordance with an event trigger. For example, a window may be defined when a patient-related event occurs (e.g., when the patient's temperature exceeds a pre-determined value). In some embodiments, a window may be defined according to a combination of 1) a triggering event and 2) a pre-determined period of time.

The pipeline method 220 may include labeling the data with ICU and/or death labels (block 230). The pipeline method 220 may include imputing missing values (block 232). The pipeline method 220 may include calculating time series features (e.g., exponentially-weighted moving average, rolling standard deviation, etc.) (block 234). The output of the preprocessing step 224 may be a data set (e.g., a hierarchical data set, a nested data set, a flat file data set, etc.). The pipeline method 220 may be performed by the processor 160 executing instructions stored in the memory 162 of the server 102. Specifically, the model training module 168 of the server 104 may perform the preprocessing and training. The input (e.g., EHR) and the output of the pipeline method 220 may be stored in a database, such as the database 108 of FIG. 1.

The pipeline method 220 may include training a ML model using the data preprocessed in the block 224 (block 236). Specifically, training the ML model may include training a gradient boosting tree using windowed data (where, as used herein, "windowed data" refers to data collected over corresponding window of time) from one or more years until a condition is met (e.g., until a precision-recall area under curve (PR-AUC) does not improve for 10 training iterations) (block 238). In embodiments wherein the model utilizes a gradient boosting tree, no mean imputation may be necessary. This is because gradient boosting tree algorithms typically do not require imputation, because such algorithms are able to learn how to split in the presence of a missing value. However, because data is generated by clinicians who use reason to determine which data to collect, caution needs to be taken to avoid raising false alarms. To this end, some missing values may be imputed using the present techniques to effectively assume the patient's levels are "normal".

In general, the present techniques are designed for seamless integration into any setting (e.g., formal clinical settings such as hospitals, informal setting such as home care, etc.). Special consideration was made during the training phase of the present techniques to ensure that it is agnostic to the data collection policies of the setting in which it is used. For example, the present techniques make predictions based on the values for each test, not factoring in the significance of whether a value is taken or missing. Missing labs correlate with the patient's condition; however, they are susceptible to change for a number of reasons. Also, changes in a hospital's policy can affect which labs are routinely taken. Attitudes of clinicians toward testing, or personal preference of individual practitioners can also affect which labs are taken, regardless of the patient's condition. If the model factors in which labs are taken, and the number of missing labs changes for any reason, the efficacy of its predictions could decline because the model learned to make its prediction based on the presence or absence of a lab and not its value.

Furthermore, certain labs are only taken when a patient has a severe condition, thus only the sicker patients receive those labs. If missing values are included in predictive power, ordering those labs would alarm that the patient's condition is worsening, regardless of the lab results. The outcome of this would be that a patient getting an uncommon lab would appear sick even if the lab value was normal. Similarly, there would be little change in the deterioration score of a patient who had an abnormal value for an infrequent test that later returned to normal. This is because the presence of the labs being taken is correlated with sicker patients. This would also be confusing to clinicians who would see the infrequently ordered labs as important values, even if those values returned normal. Stated differently, for less common labs, the mere presence of a lab observation may have a greater influence on a patient's risk score than the presence of a favorable/unfavorable clinical value relating to that lab.

For instance, clinicians tend to test sicker patients lactate levels, while not testing those of healthier patients. Therefore, sicker patients tend to have lactate tested while healthier patients do not. This presents itself as a problem at runtime because the model realizes that patients tested for lactate are in a more serious condition. The clinician would only see that lactate seems to be a useful test value. If the clinician starts ordering lactate testing because of the importance of lactate testing to the model, the model would start to flag more patients as deteriorating. The lactate lab could raise false alarms on patients even if the patients' labs came back normal. FIG. 2D includes a bar chart 290 depicting the relative importance of some features/variables in determining a patient's risk score.

The asymmetry of features may be corrected for at runtime, in some embodiments. For example, if the clinician knows that lactate is an important piece of information for the model, then the clinician may be more likely to order the lactate lab for patients when they would not have otherwise. If care is not taken during training of the model to account for such actions by clinicians, then the model may only learn that the presence of a lactate value is a signal of a sick patient and thus raise the deterioration score corresponding to the patient regardless of the value of the test.

To mitigate these effects, the present techniques apply a technique not known in the prior art of filling in missing values for uncommon labs (e.g., lactate, phosphorus, etc.) with random values taken from the normal range/empirical distribution. This imputation is based on an assumption that the patient's levels are "normal", with the same variability that we see throughout rest of the dataset. This training step may be required in embodiments of the present techniques using a nonlinear classifier. For embodiments using a linear classifier, a mean imputation may not cause this training artifact, and such mitigation may not be necessary. The present techniques may include impute the mean for rare labs like lactate during testing and a runtime. The present techniques may also include imputing the least common categorical features with the normal value. In embodiments using a nonlinear classifier, designating multiple classes for target variables may not improve performance. The set of uncommon labs may be identified using any suitable technique (e.g., via regression analysis of EHR). Whereas the present techniques may impute values with random values sampled from an empirical distribution of the training dataset, prior art techniques (e.g., linear model-based techniques) may merely impute a mean/median value of the training data.

By imputing missing values, the modeling is made much more robust. As noted above, the present techniques may be implemented successfully using lab values that are already collected for a majority of patients in most settings (e.g., disparate hospital systems). The passivity of the present techniques and careful imputation process ensures that clinicians do not need to make any changes to their current workflow or practices, and that the program may continue to make accurate predictions even if policy changes are put into place that alter which tests are routinely ordered. In general, the present techniques are easy to implement, simple to interpret, and robust to change.

The pipeline method 220 may include evaluating the receiver operator characteristic area under curve (ROC-AUC) and PR-AUC at each window over a time span (block 240). The pipeline method 220 may further include tuning hyperparameters using a subset (e.g., 10%) of the training data (block 242). The present techniques may also include calculating permutation importance to determine which features are globally important. Using this information, features with low predictive power may be filtered out, and the model may be retrained on only the most important features.

Figure 2C:
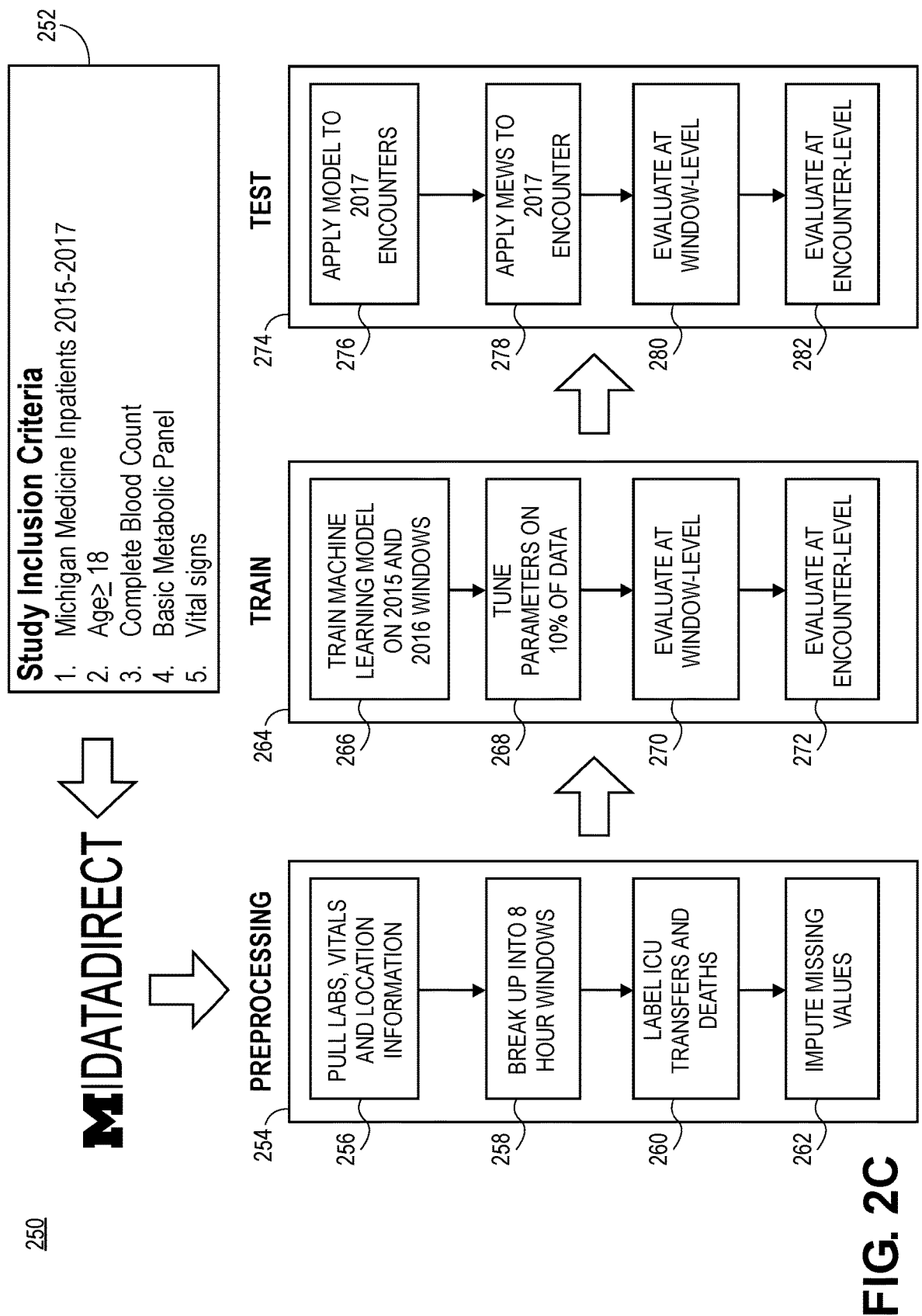
FIG. 2C depicts an example pipeline method for training and validating a model using the present techniques.
Figure 2D:
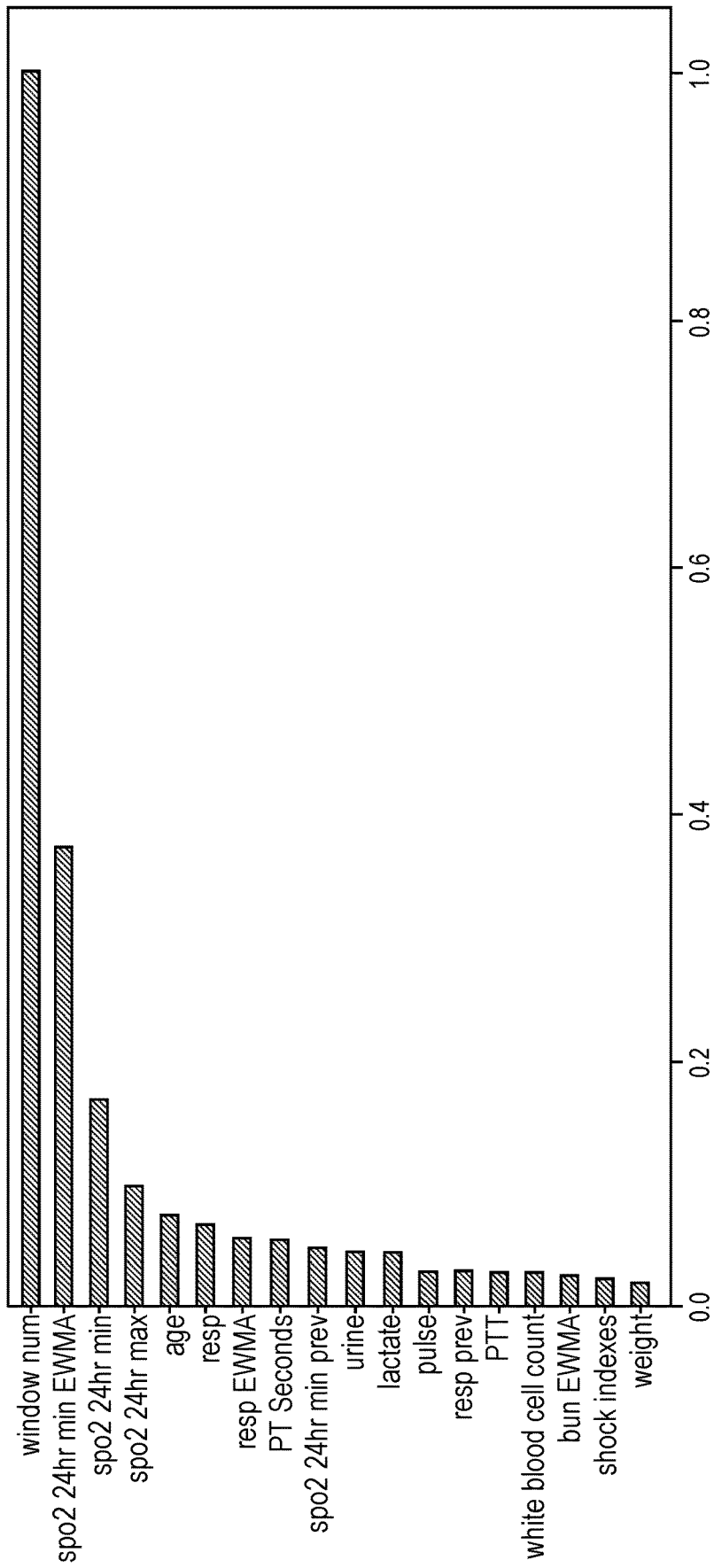
FIG. 2D is a chart depicting the relative importance of a subset of features/variables in determining a patient's risk score.

FIG. 2C depicts an example pipeline method 250 for training and validating a model using the present techniques. The pipeline method 250 may include gathering study participant EHR data based on a number of criteria (block 252). The pipeline method 250 may include preprocessing the EHR data (block 254). Preprocessing may include pulling labs, vitals, and location information corresponding to the respective patients/study participants (block 256), in addition to past medical history and location information of the patient. Past medical history of the patient may include information relating to chronic conditions of the patient (e.g., asthma). Location information may include the patient's country, address, zip code, latitude/longitude, etc.

The 250 method may further include breaking up the EHR data into windowed intervals, as discussed above (block 258), labeling the EHR data using a plurality of outcome labels (e.g., ICU transfer, death, etc.) (block 260), and imputing missing values (block 262). The pipeline method 250 may include training a model (block 264). Training the model may include training an ML model using one or more years of the windowed EHR data (block 266), tuning parameters on a subset of the EHR data (block 268), evaluating the EHR data at the window level (block 270), and evaluating the data at the encounter level (block 272). The pipeline method 250 may include testing the model (block 274). Testing may include applying the model to a validation data cohort disjoint from the data set used to train the model (block 276), applying MEWS to the disjoint data (block 278), evaluating the data at the window level (block 280), and evaluating the data at the encounter level (block 282). For example, in some embodiments, the method 200 makes a new prediction each time a vital sign is taken. In other embodiments, the method 200 makes a prediction only once within a window of time.

Figure 2E:
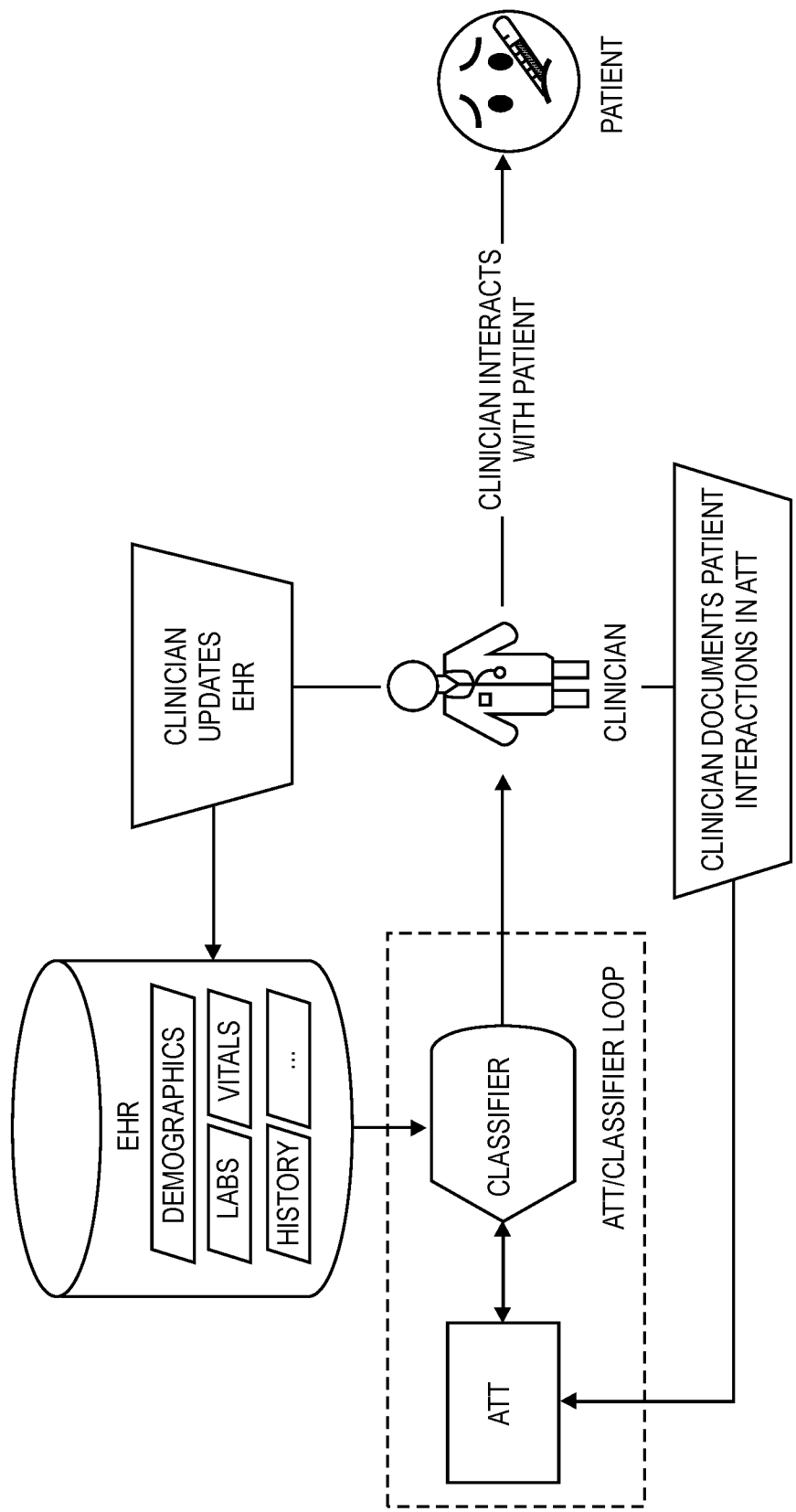
FIG. 2E is a flow diagram depicting an example method of using a classifier and tuning algorithm in the provision of care.

FIG. 2E depicts an example flow diagram representing an example method 295 for the provision of care using the system 100 of FIG. 1. FIG. 2E. In FIG. 2E, ATT (e.g., an RL algorithm) tracks the output of a classifier and accepts input from a clinician corresponding to whether an intervention, as discussed herein, was administered to a patient. The algorithm tunes an alarm threshold for the classifier.

Figure 2F:
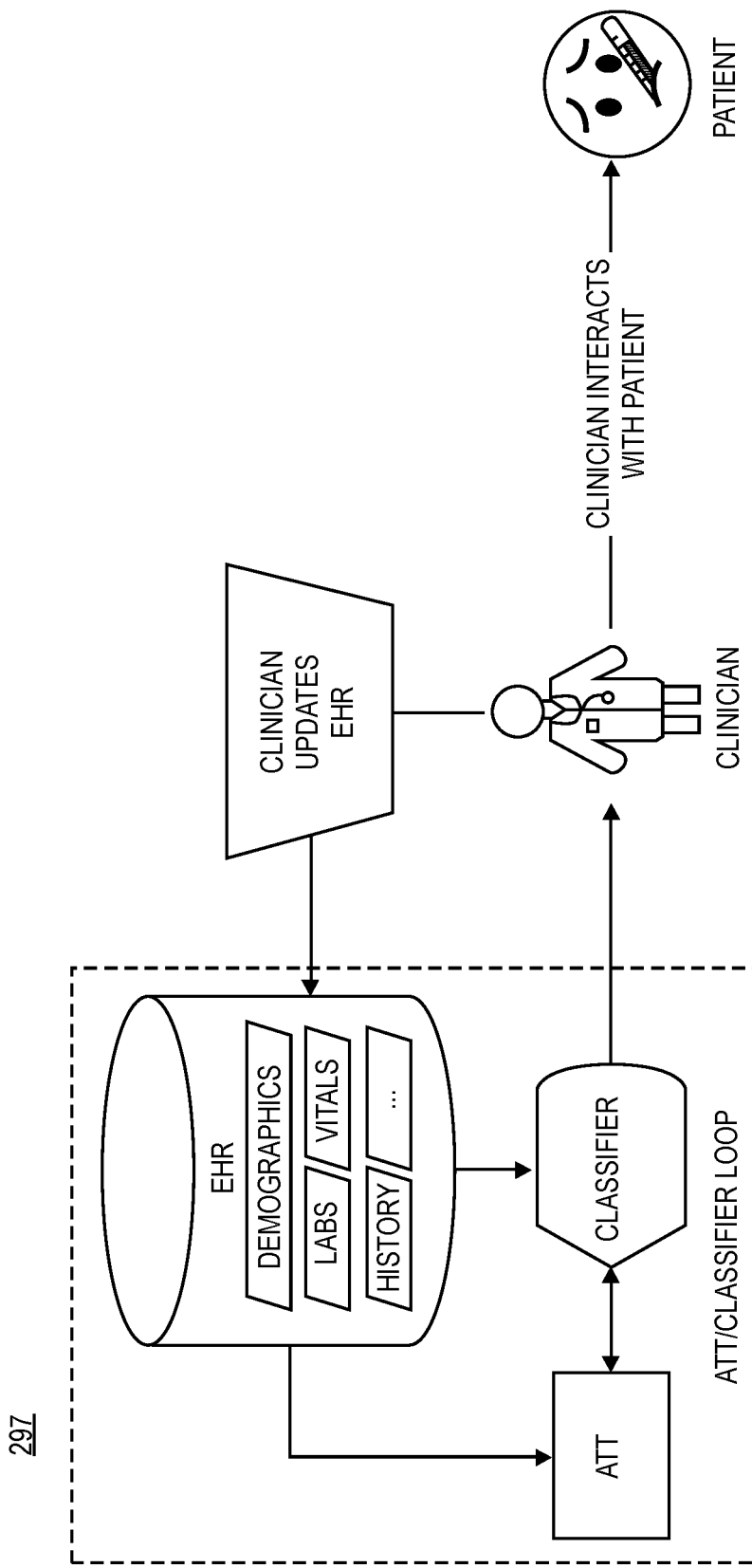
FIG. 2F is a flow diagram depicting an example method of using a classifier and tuning algorithm in the provision of care.

FIG. 2F depicts an example flow diagram representing an example method 297, wherein ATT (e.g., a RL algorithm) monitors EHR data (e.g., the database 180) to determine whether an intervention is administered to a patient, in addition to timestamped output of a classifier. The algorithm tunes an alarm threshold for a classifier based on whether or not the clinician administered an intervention.

Example Window-Based Lab Analysis

It should be appreciated that one of several techniques may be used to sample patient conditions. At a high level, a patient may be associated with one or more encounter, generally defined as a longer-term time measurement of the patient, such as a visit to a hospital (whether during inpatient or outpatient care). The encounter may be subdivided into a plurality of windows, wherein each window is a subdivision of the overall encounter of the patient. At an even more granular level, a window for a patient may be subdivided further into one or more observations corresponding to discrete care events (e.g., the taking of a patient's vital signs by a clinician). The combination of encounters, windows, and observations provide non-mutually exclusive time-based frames of patient care, and a respective ROC-AUC value may be determined at each time frame. Nonetheless, sick patients usually stay in the clinical setting for a period of time longer than an observational period. Therefore, the most useful frame may be window-based. The present techniques may include a method and system for automatically dividing time of day into windows, based on a default time division or an event, as noted above. An observation of a patient may be gathered manually, by a health care provider or staff member. In some embodiments, observations may be automatically gathered (e.g., by a medical device, a sensor, etc.). In some embodiments, a pre-determined number of observations may be automatically gathered within each window of time. For example, a system may include computer-executable instructions that when executed cause sixty observations per window to be collected. When the window length is set to one minute, the system may collect one observation once every second. When the window length is set to one hour, the system may collect an observation once every minute. The system may include computer-executable instructions for associating each observation with one or more of (i) the patient (ii) a window identifier, and (iii) an absolute time stamp.

In a window-based embodiment, a plurality of scores (e.g., an ROC-AUC) of a patient may be measured at window intervals several times per day, and the worst value selected from the plurality. In this way, the present techniques avoid biasing sick patients who, because they are observed more frequently within a given window, are associated with a higher sampling rate. The process of comparing sick and healthy patients is thus made fairer by windowing observational data and selecting one observation per window.

As discussed with respect to FIG. 2A, normalizing patient EHR may include subdividing each patient's time in care into discrete windows. As noted in block 228 of FIG. 2, the windows lengths may evenly divide a 24-hour period. For example, three eight-hour windows may be chosen, or 48 30-minute windows may be chosen, or six four-hour windows, etc.

Figure 3:
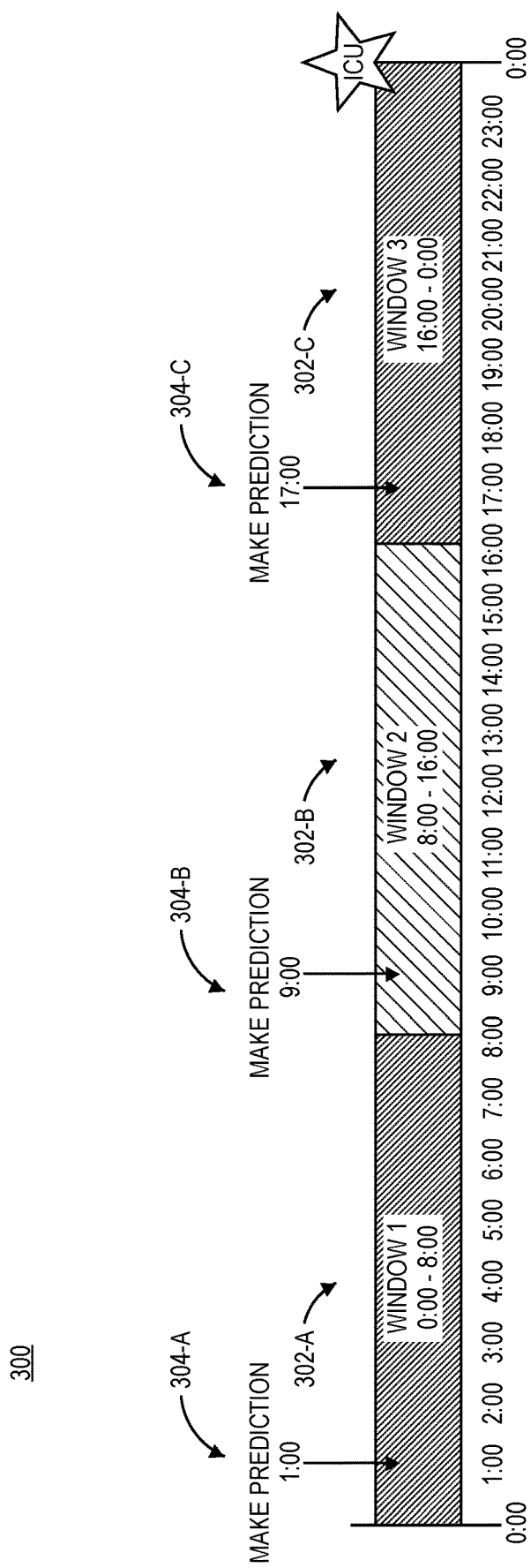
FIG. 3 depicts a block diagram showing an exemplary window.

FIG. 3 depicts a block diagram showing an exemplary window 300. Window 300 may be divided into three windows 302. The three windows 302 may each include one or more feature values 304 set to the earliest time value after the start of the window up to one hour past the start of the window. For example, the feature value 304-B begins at 09:00, which is one hour after 08:00, the start of the window 302-B. Within each of the windows 302, a prediction is calculated. If any values are missing from the windows 302, then the most recent values from the previous time interval are used. An exponentially weighted moving average with a minimum period of four windows (corresponding to just over one day for eight-hour windows) and $\alpha=0.4$ and a rolling standard deviation for each continuous feature may be included. A one-time step lag may be added to each feature. When a feature is missing for a window, then the value from the previous window may be carried forward to the current/next window.

User-Defined Thresholds/Learned Thresholds

In an embodiment, the present techniques may generate alarms corresponding to specific patients when a risk score threshold is met. For example, a given patient may receive a risk score of 8, wherein any risk score over 7 results in the generation of an alarm. A classifier may be used to generate the risk score, wherein the classifier analyzes the EHR of the patient as discussed above. A process interpreting the output of the classifier (e.g., the risk score) may determine whether to alert a clinician that a patient is deteriorating based on the risk score and one or more thresholds. The lower the threshold, the higher the chance that an alarm may relate to a false positive. Current techniques for updating such threshold values require a tremendous amount of time and effort, and in some cases, are unable to compute such threshold values.

The present techniques include methods and systems for learning the threshold for an alarm automatically. In an embodiment, ATT (e.g., a RL technique) tunes the threshold for making predictions in a systematic way and then tracks clinician behavior. For example, a clinician's behavior may include the ordering an antibiotic drug (i.e., an intervention). As the threshold is lowered, more false alarms are generated. As the number of false alarms rises, the clinician may eventually ignore the alert. When ATT determines that the clinician is ignoring more true alarms due to alarm fatigue, the technique will raise the threshold. The technique may measure alarm fatigue by, for example, analyzing the relationship between risk scores, interventions performed, and later outcomes. For example, if given cohort of patients experience a high number of risk scores, and few interventions are performed, and the patients later experience rapid deterioration (e.g., as measured by ICU trips within a given number of hours after the non-intervened observation).

The classifier is exposed to more scenarios, makes more predictions and the subsequent trajectory of each patient is recorded, ATT can then determine an optimal level for the threshold based on the attitudes of practitioners. This allows for a more precision response based on the practices of a particular setting (e.g., a hospital floor) as well as individual practitioners. It should be appreciated that ATT is a technique for updating a threshold dynamically, not for updating the predictive model. However, the predictive model output may be used in conjunction with the threshold value to determine whether to take specific actions (e.g., generate an alarm).

In some embodiments, a tradeoff may exist between sensitivity/recall (e.g., how many of the truly sick patients the present techniques will be able to catch) and PPV/precision (e.g., the likelihood that an alarm of the present techniques will not be false). In some embodiments, a user (e.g., a clinician, administrator, or other hospital staff member) may specify a desired precision given a particular level of sensitivity by selecting point on a precision-recall curve.

Figure 4:
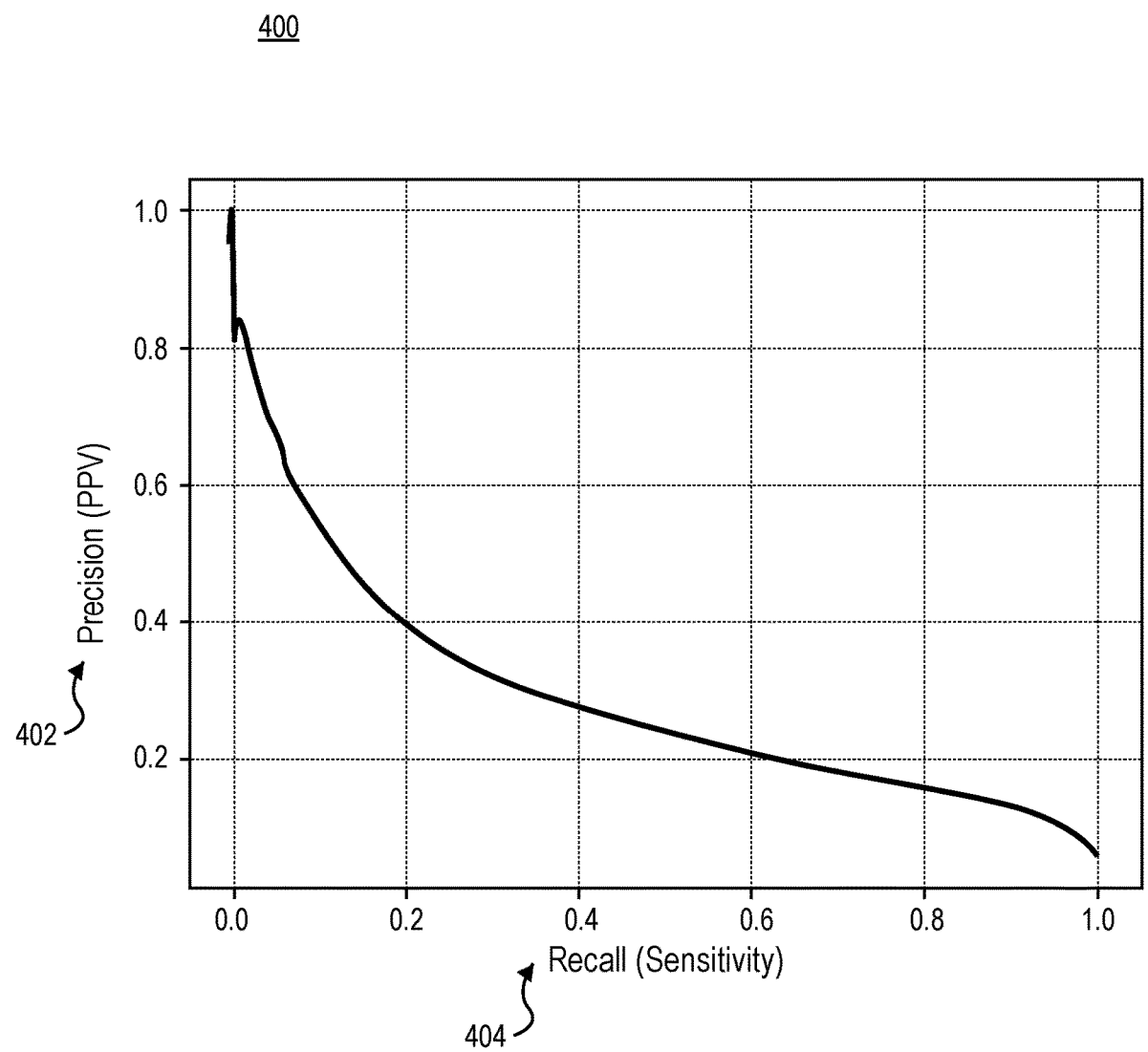
FIG. 4 depicts a precision-recall graph for visualizing and/or selecting sensitivity.

FIG. 4 depicts a precision-recall graph 400 for the present techniques that may be used 1) to allow the user to visualize the trade-off between identifying deteriorating patients and raising false alarms and 2) to allow the user to choose a prediction threshold. Graph 400 may include a first axis 402 indicating PPV and a second axis 404 indicating sensitivity.

A user of the present techniques may view a PPV/sensitivity graph like graph 400 as relates to one or more patients using a computing device. For example, a physician may use a mobile device (e.g., a smart phone) that includes a user interface displaying the most relevant vital signs for an individual patient. This user interface may help aid the clinician's decision making process for how to treat the patient.

Exemplary Vital Signs User Interfaces

Figure 5B:
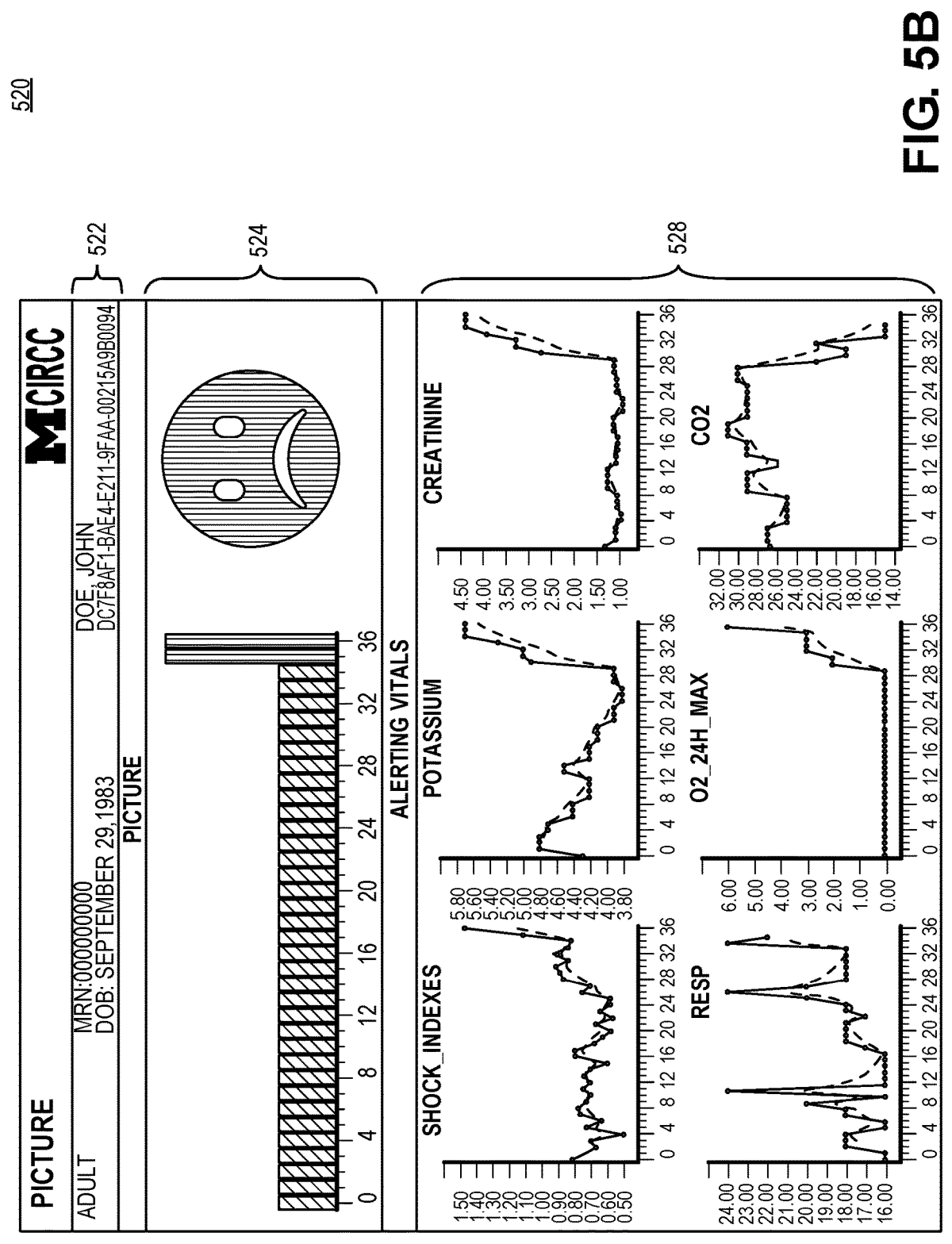
Figure 6:
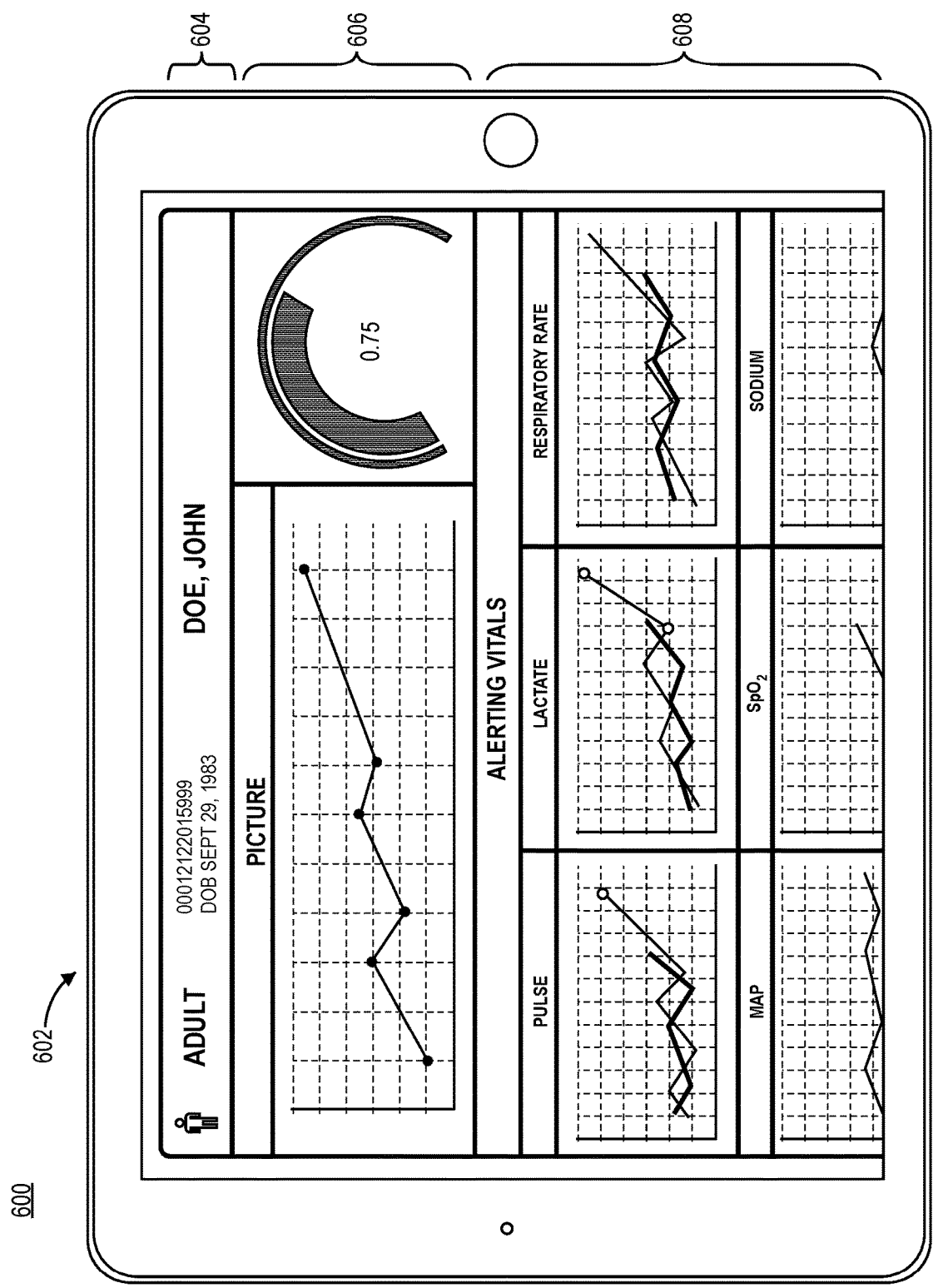
FIG. 6 depicts a graphical user interface for viewing patient vital information.

FIG. 5A depicts a graphical user interface 500 that uses scores to display a list of patients in descending order (i.e., the patients with the worst scores are displayed first). Each patient's score may differ, as depicted by the differing face values. Each patient in the list of patients may include patient attributes such as a patient identifier, date of birth, name, etc. By using the GUI 500, the clinician may quickly view the status of each of a list of patients. It should be appreciated that the GUI 500 may include additional features for allowing the clinician to quickly identify patients matching a certain criteria. For example, the clinician may reverse the sort, to view those patients whose prognosis is most favorable according to respective score. Or, the clinician may search and/or filter patients according to one or more patient attribute(s) and/or score. The GUI 500 may allow the clinician to search the score representationally (e.g., according to a face value) or a raw value, as depicted in FIG. 6. In general, the GUI 500 may display any suitable representation of the risk score. Moreover, the clinician may select one of the patients in the patient list of the GUI 500 to retrieve specific information as to the patient's condition as depicted in FIG. 5B. The clinician may use the GUI 500 to quickly determine which patient is most in need of care, which in turns helps the supervisory clinician to more effectively allocate the time and resources of subordinate clinicians (e.g., lab technicians, nurses, etc.).

FIG. 5B depicts a graphical user interface 520 that uses SHAP values to display the most relevant vital signs for a patient John Doe. The GUI 520 may be displayed as a result of the clinician selecting a particular patient (e.g., John Doe) from the list of patients in the GUI 500. The GUI 520 includes a biographical information section 522, a visualization using a patient trajectory graph 524 that includes a patient health indicator 526, and an alerting vitals inset 528 that includes a plurality of graphs relating to different patient labs wherein the plurality of graphs are ordered according to respective SHAP value. For example, in the depiction of FIG. 5B, the alerting vitals inset 528 is displayed in a row-major left-to-right ordering from most to least critical SHAP value. For example, the SHOCK INDEXES graph corresponds to the most critical SHAP value, and the $CO_2$ graph corresponds to the least critical SHAP value. It should be appreciated that any suitable means for displaying the respective SHAP values of the patient's alerting vitals may be used, and that other vitals may be displayed.

The GUI 500 and/or the GUI 520 may be generated by the user application 164 as a static image, web page, or other suitable format and transmitted via the network 106 to the client device 102. For example, the user application 164 may generate the GUI 520 and transmit the GUI 520 to the user application 128. The user application 168 may include computer-executable instructions that when executed cause the GUI 520 to be displayed in the user interface 124. The user application 128 may periodically receive/retrieve an updated GUI 520 reflecting the latest values relating to the patient John Doe. In some embodiments, the GUI 520 may be a web page displayed in an HTTP server executing on the server 104. The clinician may access the GUI 520 using a web browser (e.g., Internet Explorer, Chrome, Firefox, etc.) of a desktop computer implementing the client 102 and/or application (e.g., an Android application) installed in a smartphone implementing the client 102, as depicted below.

FIG. 6 depicts an alternate embodiment of the exemplary vital signs user interface in a GUI 600. The GUI 600 is implemented using a tablet or smart phone device 602, which may correspond to the client 102. The GUI 600 includes a patient biographical information section 602 corresponding to the biographical information section 522, a visualization 606 that includes a line graph indicator and a progress bar indicator corresponding to the visualization using the patient trajectory graph 504 of FIG. 5B, and an alerting vitals inset 608 ordered by SHAP value and corresponding to the alerting vitals inset 528. A clinician viewing the GUI 520 and/or the GUI 600 may be immediately able to determine the progress of a patient over time in general and with respect to individual vital measurements. As noted above, the clinician may receive alerts regarding the status of the patient (e.g. John Doe) in the form of textual, graphical, audio, and/or vibrational alerts via the device 602.

Exemplary Prediction Explanation

In addition to supplying the end user with a patient deterioration score, some embodiments of the present techniques use SHAP to explain classifier predictions by explaining which feature(s) contribute to the predictions made by the classifier. Explaining predictions is a difficult problem for tree-based learning models and the application of SHAP is not known in existing techniques. SHAP is based on the idea of Shapley values from game-theory which aim to quantify the contribution of each player in a multi-player cooperative game. SHAP offers a strong theoretical framework and produces more consistent results as compared to simpler explanation techniques. In general, SHAP values provide an explanation of why a particular patient is deteriorating. Other methods, such as random permutation of feature values, only provide global explanations for the importance of a feature, while SHAP explains which features are driving a prediction on a per instance basis. While some linear methods are able to provide explanations, the ability to explain the predictions of nonlinear models is an unknown technique in the art. The inability of the state of the art to provide explanations for predictions generated by nonlinear models may be explained due to the fact that the ability to explain such nonlinear models is not intuitive, in the way that the ability to explain linear models is intuitive. Although the present techniques use SHAP, it should be appreciated that other suitable feature importance algorithms now existing or developed in the future may be used in some embodiments.

As noted above, for all the features, the present techniques seek to keep the system passive. This means no policy changes for data collection will need to be enforced on clinicians. Likewise, the implementation of the present techniques in a particular setting (e.g., a hospital system) will not alter the data collection practices of clinicians since the model uses values that are already collected for a majority of patients. The passivity of the present techniques, as implemented in some embodiments, ensures that the distributions of the features will not change from those of the training set due to its implementation, thus making it more robust at runtime.

The following table depicts a series of vital sign values relating to two patients, A and B. The top five variables used to determine the patients' respective risk scores are listed according to their importance, as determined/ordered by respective SHAP value. In the depicted example, the variables in the table are listed in order SHAP value with respect to a respective patient. For example, the variable 'Respiratory Rate' is listed first because it was considered the most important for Patient A due to it having the largest SHAP value (not shown). However, for Patient B, the value of 'Sodium' was considered the most influential and 'Respiratory Rate' had only the second highest corresponding SHAP value. The variables may correspond generally to those features identified in FIG. 2D:

| | Patient A | | Patient B | |
| --- | --- | --- | --- | --- |
| Variable Importance | Variable | Value | Variable | Value |
| 1 | Respiratory Rate | 32 | Sodium | 126 |
| 2 | Pulse | 130 | Respiratory Rate | 30 |
| 3 | RR Trend | 24.7 | RR Trend | 28.1 |
| 4 | Prev Day O2 Max | 3.3 | Prev Sodium | 134 |
| 5 | Today O2 Max | 15 | Chloride | 99 |

The prediction explanation feature of the present techniques has multiple advantages in the clinical setting. First, it provides a layer of transparency that allows the clinician to see why the present techniques are making a particular prediction. Thus allowing them to quickly determine the legitimacy of an alarm which will aid in mitigating the effects of alarm fatigue. In the event of a patient decline caught by the present techniques, the explanations also lend themselves to suggesting a course of treatment.

These explanations will be displayed for a clinician's review alongside the score as graphs of the lab values over the course of treatment (e.g., during a hospital stay), as depicted in FIG. 5A, FIG. 5B, and FIG. 6. The variables may be sorted in order of their importance for the individual patient, allowing the clinician to see the most important labs and the trend over time. As depicted in FIG. 2A, the clinician may provide feedback regarding the risk score, predictions, and/or explanations as the clinician uses the present techniques to interact with the patient. The clinician may be prompted by the client 102 to allow reject and/or accept a risk score, prediction and/or explanation. The client 102 may transmit the clinician's rejection/acceptance in association with an identification of a particular patient to the server 104, wherein the information may be saved (e.g., to the database 180). The clinician's responses may be used in a feedback loop, along with the subsequent trajectory of the patient, to further refine the predictive model.

Model Performance

In the medical literature, the receiver operating characteristic/area under curve (ROC-AUC) metric is traditionally used to quantify a classifier's performance. However, when the classes are extremely imbalanced the precision recall area under curve (PR-AUC) metric may be more meaningful. For example, ICU transfer and death are relatively rare events during care periods (e.g., during a hospital stay). For example, of 79,955 total patient encounters in the training, validation and test cohorts used for training and testing the models developed using the present techniques, only 8509 ICU transfers and 480 deaths were reported. Therefore, in some embodiments of the present techniques, PR-AUC was shown to be a more sensitive measure. Specifically, the PR-AUC and the ROC-AUC of several model types were tested using the validation set. A gradient boosting tree having a learning rate of 0.105, a max tree depth of 7, and a logistic objective provided a high AUC and demonstrated ability to generalize to new data. For example, a model was trained as discussed above until the PR-AUC did not improve for 10 iterations. The following includes a discussion of both the PR-AUC and the ROC-AUC that enables the present techniques to be compared and contrasted to existing published methods (e.g., eCART and Rothman). The following indicates that the present techniques appear to substantially outperform known predictive indices.

Specifically, the present techniques demonstrated a much higher PPV for a given level of sensitivity with a similar negative predictive value (NPV), as shown in the following table, wherein the NPV with respect to each row (not depicted) is nearly identical:

| | eCart | | Present techniques | |
| --- | --- | --- | --- | --- |
| Sensitivity | Specificity | PPV | Specificity | PPV |
| 0.100 | 0.995 | 0.124 | 0.995 | 0.541 |
| 0.200 | 0.981 | 0.072 | 0.981 | 0.398 |
| 0.300 | 0.962 | 0.055 | 0.960 | 0.321 |
| 0.400 | 0.933 | 0.042 | 0.933 | 0.275 |
| 0.500 | 0.893 | 0.033 | 0.898 | 0.237 |
| 0.600 | 0.834 | 0.026 | 0.854 | 0.207 |
| 0.700 | 0.754 | 0.020 | 0.799 | 0.181 |
| 0.800 | 0.653 | 0.017 | 0.728 | 0.158 |
| 0.900 | 0.441 | 0.012 | 0.623 | 0.132 |

It should be noted that for a given level of specificity, the present techniques provide a much higher PPV than eCart with a similar NPV. This higher PPV translates to fewer false alarms in a clinical setting (e.g., on a hospital floor). It should also be appreciated that the PPVs provided above are examples, and that in practice, more strongly correlative PPVs have been achieved.

Figure 7:
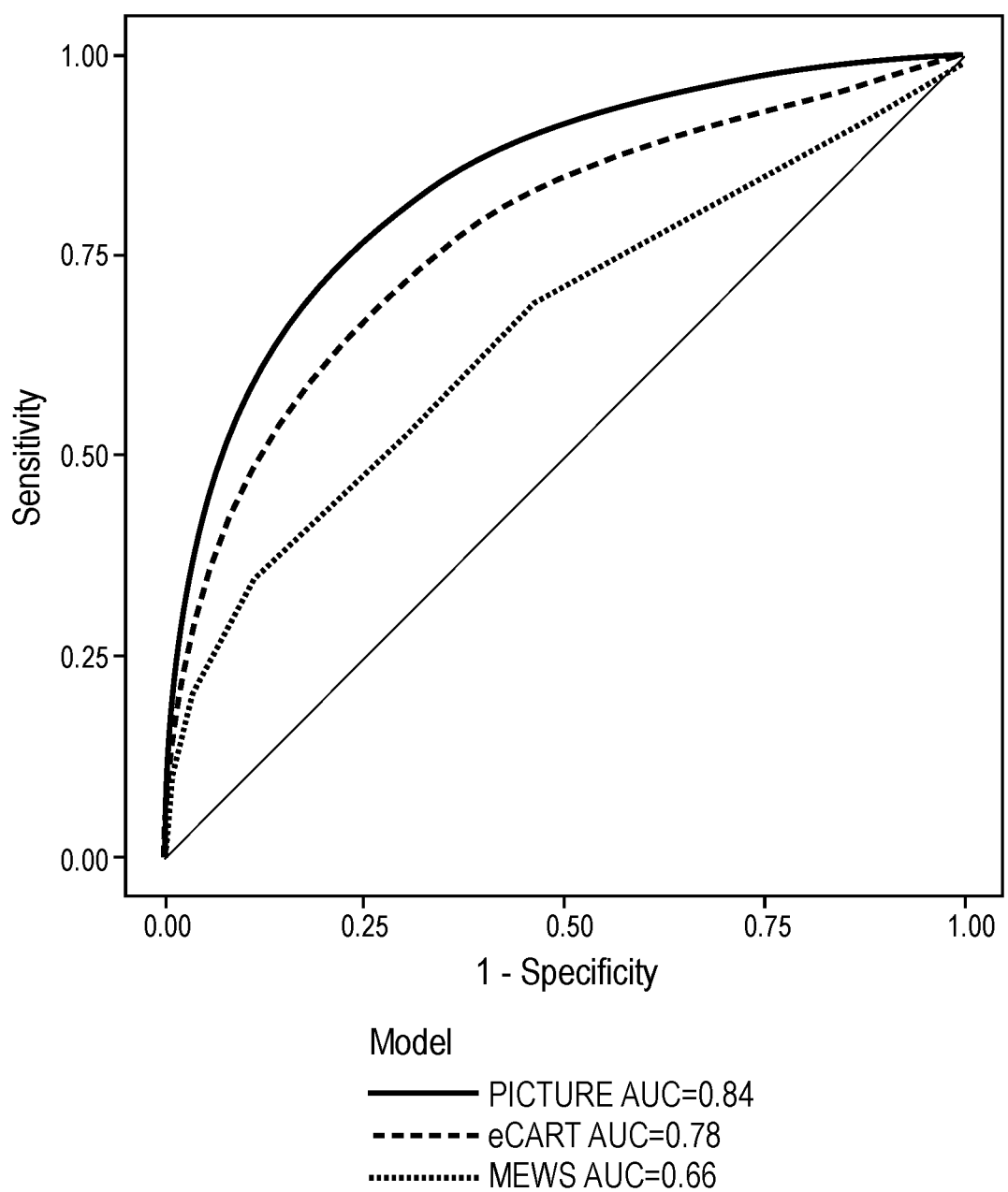
FIG. 7 depicts respective receiver operating characteristic curves comparing the present techniques to known techniques.
Figure 8:
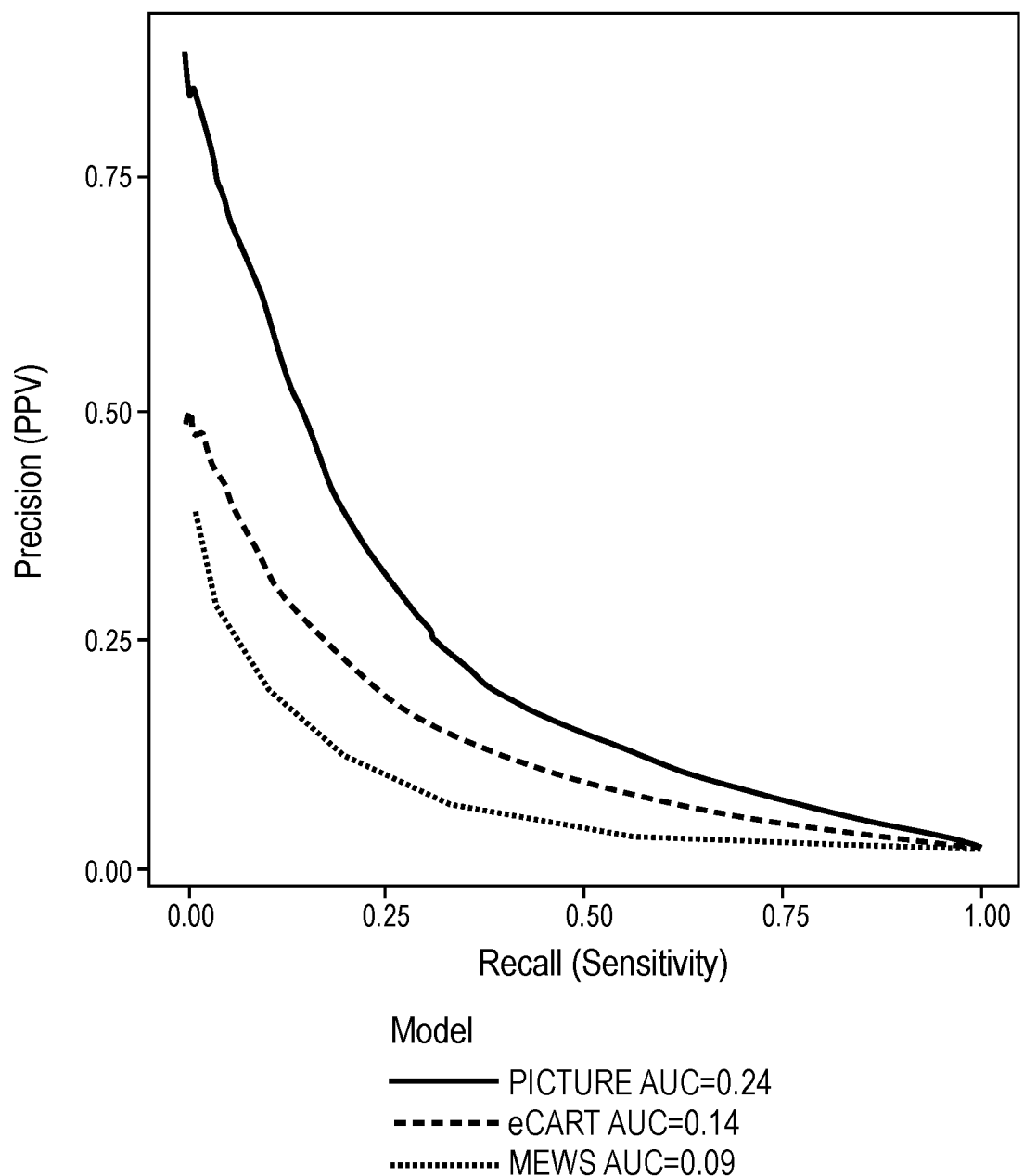
FIG. 8 depicts the respective precision/recall curves comparing the present techniques to known techniques.

To increase comparability with state of the art published methods, the ROC-AUCs and PR-AUCs for predicting an adverse event within 24 hours of each observation are also provided. FIG. 7 depicts the respective ROC curves for the present techniques, eCart, and MEWS. FIG. 8 depicts the respective PR curves for the present techniques, eCart, and MEWS. In every metric, the present techniques performed better than existing measures of patient risk. Specifically, FIG. 7 demonstrates that the present techniques had a higher ROC-AUC than any other measure of patient risk and FIG. 8 demonstrates that the present techniques had a higher PR-AUC. The following table depicts ROC-AUC AND PR-AUC measures for predicting an adverse event within 24 hours of each observation for MEWS, eCart and the present techniques:

| Model | ROC-AUC | PR-AUC |
| --- | --- | --- |
| MEWS | 0.66 | 0.09 |
| eCart | 0.78 | 0.14 |
| Present techniques | 0.84 | 0.29 |

Additional Capabilities

As noted above, any information about the patient's health may be analyzed via EHR to determine the patient's score. All that is known to the techniques herein (e.g., the system 100) about the patient may be considered a possible contributor to that patient's score. This includes all past comorbidities (e.g., heart failure, cancer, diabetes, renal failure, chronic obstructive pulmonary disease, asthma, hypertension, organ transplant, etc.) as well as past scores. The use of a patient's information from previous encounters allows the present techniques to tune the conception of 'baseline' to the individual. This again allows for a more precision response by the present techniques. For example, because many patients are discharged and re-admitted within the same health system, some embodiments of the present techniques may include determining a score for a patient in light of a previous score at the time the patient is readmitted (i.e., a score history). A readmitted patient may have a baseline score (e.g., the last available score from the previous admittance), or an aggregated value (e.g., an average score over the last N windows). For example, a chronic end-stage renal failure patient may be readmitted, wherein the present techniques determine that the renal function (BUN and Cr) values are determined as negative. Further, in some embodiments, the present techniques may ingest and utilize disease states that the patient is known to have (e.g., heart failure, diabetes, cancer, chronic renal failure, etc.). Such disease states may provide additional precision and over time, an individual patient can have their own precision signature that may be utilized in subsequent encounters. Therefore, when a patient is associated with multiple encounters over time, the value associated with the patient can be adaptively adjusted in an incremental way, from the previous values, rather than necessitating that the present techniques re-learn the patient's score from scratch each time. And, the present techniques may determine meaningful changes to the patient's condition based on previous scores of the patient.

The present techniques may be open ended in that additional data or feature sets can be integrated when new technologies are available. For example, combining the present techniques with high resolution features of physiologic waveform data such as heart rate variability from ECG monitoring or respiratory waveforms for respiration quality could produce significant boosting of PPV.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a central processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method of improved predicting of a patient deterioration, the method comprising:
   receiving, via one or more processors, an electronic health record data set of the patient,
   determining, via one or more processors, a risk score corresponding to the patient by analyzing the electronic health record data set of the patient using a trained machine learning model,
   determining, via one or more processors, a threshold value by using an online/ reinforcement learning model to process input including clinician action,
   comparing, via one or more processors, the risk score to the threshold value, and when the risk score exceeds the threshold value, generating, via one or more processors, an alarm.

2. The method of claim 1, wherein receiving the electronic health record data set of the patient includes receiving at least one of derived hemoglobin oxygen saturation, heart rate, blood pressure, respiratory rate, mean platelet volume, hematocrit, hemoglobin, mean corpuscular hemoglobin, mean corpuscular hemoglobin concentration, mean corpuscular hemoglobin volume, white blood cell count, platelets, red blood cell count, and red cell distribution width, blood urea nitrogen, potassium, sodium, glucose, chloride, CO2, calcium, creatinine, age, weight, race, gender, bilirubin, partial thromboplastin time, international normalized ratio, lactate, magnesium and phosphorous, blood cultures, use of O2, Glasgow Coma Score or components thereof, urine output over past 24 hours, shock index or mean arterial pressure, chronic medical and/or surgical conditions with respect to the patient.

3. The method of claim 1, wherein receiving the electronic health record data set of the patient includes receiving at least one of labs, vitals, or location information of the patient.

4. The method of claim 1 wherein the machine learning model is either a gradient boosting tree model or a deep learning model.

5. The method of claim 1, wherein determining the risk score corresponding to the patient by analyzing the electronic health record data set of the patient includes dividing the electronic health record data set into windowed time intervals.

6. The method of claim 1, wherein determining the threshold value using the online/ reinforcement learning model includes determining the threshold value using an adaptive threshold tuning algorithm.

7. The method of claim 1, further comprising
   displaying, in a display device of a clinician, a representation of the risk score.

8. The method of claim 7, wherein displaying the representation of the risk score includes displaying one or more predictions arranged according to a feature importance algorithm.

9. The method of claim 8 wherein the feature importance algorithm is the SHapley Additive exPlanation algorithm.

10. The method of claim 1 further comprising:
preprocessing the electronic health record data set by one or more of:
a) transforming query results into a machine learning-compatible format,
b) dividing the electronic health record data into windowed time intervals,
c) labeling the data,
d) imputing missing values; or
e) calculating time series features.

11. The method of claim 10, wherein imputing the missing values includes imputing the missing values by randomly selecting values from an empirical distribution.

12. The method of claim 1, further comprising
displaying one or both of (i) the patient risk score and (ii) the alarm in a mobile computing device of a clinician.

13. The method of claim 1 wherein determining the risk score corresponding to the patient by analyzing the electronic health record data set of the patient using a trained machine learning model includes retrieving an historical risk score corresponding to the patient.

14. The method of claim 1 wherein determining the threshold value using an online/reinforcement learning model includes processing an indication made by a clinician of whether an intervention was performed with respect to the patient.

15. A non-transitory computer readable medium containing program instructions that when executed, cause the computer to:
receive, via one or more processors, a list of patients, each including a respective risk score,
display, via one or more processors, patient information corresponding to each of the list of patients in a display device, wherein the patient information is selectable, and wherein the each of the list of patients is displayed in order of SHAP value,
receive, via one or more processors, a selection made by a clinician corresponding to one of the each of the list of patients,
determine, via one or more processors, a threshold value by using an online/reinforcement learning model to process input including the selection made by the clinician,
retrieve, via one or more processors, vital sign information corresponding to the selected one of the each of the list of patients, and
display, via one or more processors, the vital sign information in the display device.

16. A computing system for predicting patient deterioration, comprising:
one or more processors, and
a memory including computer executable instructions that, when executed by the one or more processors, cause the computing system to:
receive, via the one or more processors, an electronic health record data set of the patient,
determine, via the one or more processors, a risk score corresponding to the patient by analyzing the electronic health record data set of the patient using a trained machine learning model,
determine, via the one or more processors, a threshold value by using an online/reinforcement learning model to process input including clinician action,
compare, via the one or more processors, the risk score to the threshold value, and
when the risk score exceeds the threshold value, generate, via the one or more processors, an alarm.

17. The computing system of claim 16, the memory containing further instructions that, when executed by the one or more processors, cause the computing system to:
receive at least one of derived hemoglobin oxygen saturation, heart rate, blood pressure, respiratory rate, mean platelet volume, hematocrit, hemoglobin, mean corpuscular hemoglobin, mean corpuscular hemoglobin concentration, mean corpuscular hemoglobin volume, white blood cell count, platelets, red blood cell count, and red cell distribution width, blood urea nitrogen, potassium, sodium, glucose, chloride, CO2, calcium, creatinine, age, weight, race, gender, bilirubin, partial thromboplastin time, international normalized ratio, lactate, magnesium and phosphorous, blood cultures, use of O2, Glasgow Coma Score or components thereof, urine output over past 24 hours, shock index or mean arterial pressure, chronic medical and/or surgical conditions with respect to the patient.

18. The computing system of claim 16, the memory containing further instructions that, when executed by the one or more processors, cause the computing system to:
receive at least one of labs, vitals, or location information of the patient.

19. The computing system of claim 16, the memory containing further instructions that, when executed by the one or more processors, cause the computing system to:
determine the risk score corresponding to the patient by analyzing the electronic health record data set of the patient using a trained machine learning model, wherein the machine learning model is either a gradient boosting tree model or a deep learning model.

20. The computing system of claim 16, the memory containing further instructions that, when executed by the one or more processors, cause the computing system to:
determine the threshold value using an adaptive threshold tuning algorithm.

* * * * *